(12) United States Patent
Courtois et al.

(10) Patent No.: US 9,770,400 B2
(45) Date of Patent: Sep. 26, 2017

(54) EXOPOLYSACCHARIDE FOR TREATMENT OR CARE OF SKIN, MUCOUS MEMBRANES, HAIR OR NAILS

(75) Inventors: Anthony Courtois, Morlaix (FR); Bertrand Thollas, Morlaix (FR); Raquel Delgado Gonzalez, Barcelona (ES); Juan Cebrian Puche, Barecelona (ES); Albert Soley Astals, Barecelona (ES)

(73) Assignees: Lipotec, S.A., Gava (ES); Polymaris Biotechnology, Morlaix (FR)

( * ) Notice: Subject to any disclaimer, the term of this patent is extended or adjusted under 35 U.S.C. 154(b) by 546 days.

(21) Appl. No.: 13/989,905

(22) PCT Filed: Nov. 30, 2011

(86) PCT No.: PCT/EP2011/005996
§ 371 (c)(1),
(2), (4) Date: Jul. 29, 2013

(87) PCT Pub. No.: WO2012/072245
PCT Pub. Date: Jun. 7, 2012

(65) Prior Publication Data
US 2013/0302261 A1    Nov. 14, 2013

(30) Foreign Application Priority Data
Nov. 30, 2010  (ES) .................................. 201031775

(51) Int. Cl.
| | | |
|---|---|---|
| *C12P 1/04* | (2006.01) | |
| *C12N 1/00* | (2006.01) | |
| *A61K 8/73* | (2006.01) | |
| *A61K 8/06* | (2006.01) | |
| *A61K 8/14* | (2006.01) | |
| *A61K 8/81* | (2006.01) | |
| *A61K 8/99* | (2017.01) | |
| *A61K 9/00* | (2006.01) | |
| *A61K 47/36* | (2006.01) | |
| *A61Q 19/00* | (2006.01) | |
| *A61Q 19/08* | (2006.01) | |
| *A61Q 3/00* | (2006.01) | |
| *A61Q 5/00* | (2006.01) | |
| A61K 9/107 | (2006.01) | |
| A61K 9/127 | (2006.01) | |

(52) U.S. Cl.
CPC ............... *A61K 8/73* (2013.01); *A61K 8/068* (2013.01); *A61K 8/14* (2013.01); *A61K 8/735* (2013.01); *A61K 8/8182* (2013.01); *A61K 8/99* (2013.01); *A61K 9/0014* (2013.01); *A61K 47/36* (2013.01); *A61Q 3/00* (2013.01); *A61Q 5/00* (2013.01); *A61Q 19/007* (2013.01); *A61Q 19/08* (2013.01); *A61K 9/1075* (2013.01); *A61K 9/127* (2013.01); *A61K 2800/21* (2013.01); *A61K 2800/56* (2013.01); *A61K 2800/85* (2013.01); *A61K 2800/92* (2013.01)

(58) Field of Classification Search
None
See application file for complete search history.

(56) References Cited

U.S. PATENT DOCUMENTS

| | | | |
|---|---|---|---|
| 5,455,343 A | 10/1995 | Fontaine et al. | |
| 6,436,680 B1 | 8/2002 | Guezennec et al. | |
| 2002/0187167 A1 | 12/2002 | Vacher et al. | |
| 2007/0259833 A1 | 11/2007 | Matou et al. | |
| 2008/0131472 A1 * | 6/2008 | Senni et al. | 424/423 |
| 2009/0238782 A1 | 9/2009 | Vacher et al. | |
| 2011/0245199 A1 * | 10/2011 | Senni | A61K 31/737 514/54 |

FOREIGN PATENT DOCUMENTS

| | | | |
|---|---|---|---|
| EP | 0 534 855 B1 | 4/1997 | |
| EP | 1 402 898 A1 | 3/2004 | |
| EP | 0 987 010 B1 | 9/2004 | |
| FR | 2 871 476 A1 | 12/2005 | |
| JP | 2003-313131 | 11/2003 | |
| WO | WO 98/38327 | 9/1998 | |
| WO | WO 2009/127057 | 10/2009 | |
| WO | WO 2009127058 A1 * | 10/2009 | A61K 8/73 |
| WO | WO 2010/043346 | 4/2010 | |

OTHER PUBLICATIONS

Trylagen® PCB brochure.*
Qin et al. Microbiology (2007), 153, 1566-1572.*
Rougeaux et al. Carbohydrate Research 315 (1999) 273-285.*
Petit et al. Carbohydrate Polymers, vol. 64, Issue 4 , Jun. 16, 2006, pp. 597-602.*
Xi, et al., "Advances on Pseudoalteromonas Species and Their Bioactive Compounds," Microbiology Bulletin, vol. 32, No. 3, pp. 108-112 (2004).
Elsner, P. "Antimicrobials and the Skin Physiological and Pathological Flora" in Hipler, et al., Biofunctional Textiles and the Skin, Current Problems in Dermatology, G. Burg, Ed., vol. 33, pp. 35-41 (2006).

(Continued)

Primary Examiner — Chris R Tate
Assistant Examiner — Douglas F White
(74) Attorney, Agent, or Firm — Fay Sharpe LLP

(57) ABSTRACT

A method includes administering a cosmetically or dermopharmaceutically effective quantity of exopolysaccharide of a bacterial strain isolated from *Pseudoalteromonas* sp. with deposit number CNCM I-4150 to at least one of skin, mucous membranes, hair and nails for the treatment and/or care of the skin, mucous membranes, hair and/or nails, and cosmetic and/or dermopharmaceutical compositions including the exopolysaccharide. In particular, the method and composition are suited to treatment of the aging of skin and for the treatment and/or care of disorders, conditions and/or diseases which are a result of a lack or decrease in hydration.

28 Claims, 1 Drawing Sheet

(56) References Cited

OTHER PUBLICATIONS

Gottschalck, et al. "International Cosmetic Ingredient Dictionary and Handbook" Twelfth Edition, vol. 3, pp. 3040-3065 (2008).
Haug, et al. "Coated Textiles in the Treatment of Atopic Dermatitis", in Hipler, et al., Biofunctional Textiles and the Skin, Current Problems in Dermatology, G. Burg, Ed., vol. 33, pp. 144-151 (2006).
Kamerling, et al. "Characterization by Gas-Liquid Chromatography-Mass Spectrometry and Proton-Magnetic-Resonance Spectroscopy of Pertrimethylsilyl Methyl Glycosides obtained in the Methanolysis of Glycoproteins and Glycopeptides", Biochem. J., vol. 151, pp. 491-495 (1975).
Malcolm, et al. "Controlled release of a model antibacterial drug from a novel self-lubricating silicone biomaterial", J. Controlled Release 97, pp. 313-320 (2004).
Matuoka, et al. "A decrease in hyaluronic acid synthesis by aging human fibroblasts leading to heparin sulfate enrichment and growth reduction" Aging vol. 1, No. 1, pp. 47-54 (1989).
Raguenes, et al. "*Alteromonas infernus* sp. nov., a new polysaccharide-producing bacterium isolated from a deep-sea hydrothermal vent" J. Applied Microbiology vol. 82, pp. 422-430 (1997).
Raguenes, et al. "*Vibrio diabolicus* sp. nov., a New Polysaccharide-Secreting Organism Isolated from a Deep-Sea Hydrothermal Vent Polychaete Annelid, *Alvinella pompejana*" Intl. Journal of Systematic Bacteriology, vol. 47, No. 4, pp. 989-995 (Oct. 1997).
Rougeaux, et al. "Structure of the exopolysaccharide of *Vibrio diabolicus* isolated from a deep sea hydrothermal vent" Carbohydrate Research 332, pp. 40-45 (1999).
Schaab, C. "Impregnating Fabrics with Microcapsules" HAPPI, pp. 84-86 (May 1986).
Volpi, et al. "Low molecular weight Heparin (5 kDa) and Oligoheparins (2 kDa) Produced by Gel Permeation Enrichment or Radical Process: Comparison of Structures and Physicochemical and Biological Properties" Analytical Biochemistry vol. 200, pp. 100-107 (1992).
"HYADISINE™: Retains water to smooth the skin," pp. 1, Retrieved from http://www.sofw.com/index/sofw_en/softw_en_product_launch_pad . . . on Jan. 24, 2013 (XP-002690983).
Nelson, G. "Application of microencapsulation in textiles", Intl. Journal of Pharmaceutics 242, pp. 55-62 (2002).
Mancuso, et al. "Bacterial Exopolysaccharides from Extreme Marine Environments with Special Consideration of the Southern Ocean, Sea Ice, and Deep-Sea Hydrothermal Vents: A Review" Marine Biotechnology, vol. 7, pp. 253-271 (2005).
Gottschalk, et al. "International Cosmetic Ingredient Dictionary and Handbook", The Cosmetic, Toiletry and Fragrance Association, 2008, 12th Edition, vol. 3, pp. 3040-3064 (resubmitted).

\* cited by examiner

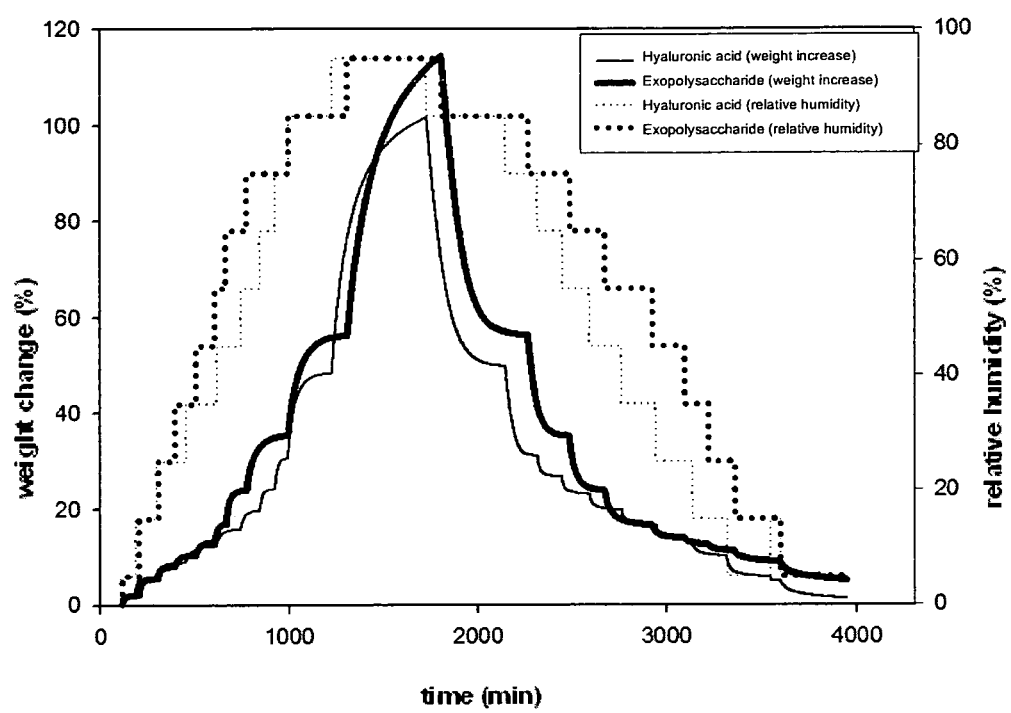

US 9,770,400 B2

EXOPOLYSACCHARIDE FOR TREATMENT OR CARE OF SKIN, MUCOUS MEMBRANES, HAIR OR NAILS

CROSS REFERENCE TO RELATED APPLICATIONS

This application claims priority from PCT Application Serial No. PCT/EP2011/005996, filed on Nov. 30, 2011, which claims the benefit of Spanish Application No. P201031775, filed on Nov. 30, 2010, the disclosures of which are incorporated herein by reference in their entireties.

FIELD OF THE INVENTION

This invention relates to an exopolysaccharide (EPS) excreted by bacterial strain CNCM I-4150 of the *Pseudoalteromonas* sp species. This invention also relates to the use of this exopolysaccharide in cosmetic or dermopharmaceutical compositions for the treatment and/or care of the skin, mucous membranes, hair and/or nails.

BACKGROUND

The skin, mucous membranes, hair and/or nails constitute a physical barrier between the organism and its environment. The skin is composed of two tissues: the epidermis and the dermis. The epidermis is the outermost layer of the skin which is impermeable and therefore provides protection from external agents. It is a keratinized pluristratified epithelium which is continually renewing itself. Keratinocytes constitute the principal population of cells in the epidermis and are responsible for maintaining the epithelial structure due to their function as a barrier.

The epidermis is composed of several cell layers: basal stratum which is the deepest layer connected to the dermis in the dermal-epidermal union and is composed of undifferentiated cells. Over time, these cells differentiate and migrate towards the surface of the epidermis, constituting the different layers. The uppermost layer formed is the stratum corneum which is composed by the corneocytes. The corneocytes are keratin-rich cells which are capable of retaining water, and are surrounded by a protein and a lipid shell. There are from 10 to 30 layers of stacked corneocytes, which are connected to each other by protein bridges called desmosomes. The resulting structure is a natural physical barrier of skin which retains water. Corneocytes are dead cells which are eliminated by desquamation, and which, in the absence of water, do not desquamate normally leading to a dense, dry and rough skin appearance. The loss of the superficial stratum caused by desquamation is compensated by the migration of cells from the basal stratum towards the surface of the epidermis. This is, therefore, a process of continual renewal of the skin which helps to keep it soft.

The corneocytes contain a protein called filaggrin which binds to keratin proteins. Filaggrin is located in the outer part of the corneocytes, whilst keratin, which is capable of retaining water, remains in the inner part of the corneocytes. When the humidity content of the skin decreases, specific proteolytic enzymes of the corneum stratum cause the rupture of filaggrin in free amino acids in order to control the osmotic pressure of the skin and the quantity of water that it contains. All these free amino acids are produced together with other physiological chemical products such as lactic acid, pyrrolidone, carboxylic acids, urea and other salts present in the corneum stratum, called "natural hydration factors" which are responsible for maintaining the skin moist and flexible by attracting and retaining water. The content of water in the corneum stratum under physiological conditions is normally close to 30%. The "natural hydration factors" are water soluble intercellular substances that undesirably can easily leave the skin thus decreasing its concentration, which leads to water not being so easily bound in the epidermis.

The dermis is the layer of skin located under the epidermis and firmly connected to it. It is an elastic support tissue of mesodermal origin which is mainly constituted of fibroblasts and an extracellular matrix of fibrous proteins (collagen and elastin) and non-fibrous proteins (proteoglycans and glycoproteins). The dermis, which is essentially rich in hyaluronic acid and polysaccharides, works as a reserve of water, retaining the water brought to it by the blood vessels. It stores water like a sponge and passes water to the epidermis when is needed, together with other the nutritional substances the epidermis may also need. Therefore, the dermis plays a fundamental role in the development and differentiation of the epidermis. The fibroblasts and the extracellular matrix also influence on the mechanical properties of the skin, in particular, its elasticity, tone and firmness, as well as the skin's density.

The skin can lose water in two ways: mainly through transpiration, which is an active phenomenon caused by the sweat glands to regulate the temperature of the skin, and also, although minimally, by passive evaporation of water through the epidermis. This passive evaporation or insensible water loss takes place with a kinetics that is the reflection of a balance between the water content of the epidermis and the relative humidity of the surroundings, and its measurement is the reflection of the integrity of the skin's barrier. For example, in normal conditions insensible water loss is usually 5 $g/m^2$/hour but in atopic children, and in areas of dry skin without eczema insensible water loss can reach 13 to 18 $g/m^2$/hour.

The integrity of the skin's barrier or the skin's barrier function also depends on the density of the corneum stratum. The corneum stratum has been compared to a brick wall in which the keratinocytes or corneocytes (bricks) are the essentially protein non-continuous portion, terminally differentiated, which are embedded in a continuous matrix of specialized lipids (mortar). The lipids provide the essential element of the barrier to water, and the corneocytes protect against continual abrasion by chemical or physical injuries.

Hydration is an essential factor in the maintenance of the skin's youthfulness and vitality for any age group. When the quantity of water is insufficient, the stratum corneum loses elasticity and experiences a sensation of tightness, a phenomenon which is usually referred to with the term "dry skin". However, properly hydrated skin is soft, flexible and has a young, glowing look.

Healthy skin is that which maintains ideal water concentration levels. The presence of water in the dermis and epidermis favors the group of regenerative mitotic reactions of the cutaneous cells, which contribute to the regeneration of our skin. An optimal water concentration is decisive for the flexibility of the skin and, as a consequence, for the prevention of the appearance of wrinkles caused by age and their treatment, and for the healing of small wounds.

However, homeostasis of the skin can be affected by certain physiological factors (age, menopause, hormonal changes, lack of nourishment and lack of hydration, xerosis, etc.) or environmental factors (ultraviolet radiation, pollution, stress, hypoxia, infectious agents, dry weather conditions, irritants, etc.). These factors cause the decrease of an assimilation and fixation of water in the skin which quickly becomes obvious on the cutaneous surface through unmistakable signs such as dry skin or a tendency to irritation. This leads to a decrease in the regeneration of the epidermis (the cells in the basal stratum are less actively divided, the proteins in the skin are denatured and disrupted, and/or the protective intercellular lipid layers are eliminated and cohesion between the cells is reduced) which leads to a decrease in the skin's hydration. Environmental factors also cause deregulation of the hair and nails' hydration, both becoming rough, fragile and brittle.

The cosmetic and dermopharmaceutical industry has undertaken considerable efforts to develop compounds which are capable of maintaining the water balance of the skin, mucous membranes, hair and/or nails, with the objective of improving its appearance, as well as its protective function and function as a barrier. One of these ingredients is hyaluronic acid; an unsulfated glycosaminoglycan of the extracellular matrix formed by D-glucuronic acid and D-N-acetylglucosamine. Hyaluronic acid is capable of retaining water in the skin, helping to maintain the skin more hydrated, elastic and with a more uniform cutaneous surface. The amount of hyaluronic acid which synthesizes the skin drastically reduces with age (Matuoka et al. *Aging*, 1989, 1(1):47-54) and this is the cause of the tendency of mature skin to dry out, to lose elasticity and to form wrinkles. Hyaluronic acid plays an important function in the prevention and decrease both wrinkles and expression lines; one of the more commonly employed strategies by the cosmetic and dermopharmaceutical industry for the treatment of wrinkles is the administration of hyaluronic acid both topically and subcutaneously due to its capacity of water absorption and therefore fill the wrinkle from inside the skin.

Hyaluronic acid is found in the extracellular matrix of human and animal tissues, but it also exists in certain strains of bacteria such as those of the genus *Streptococcus* and *Pasteurella*, which produce it by emulating animal tissues as a way of protecting themselves against attack from the immune system of the animals they infect, as they are pathogenic microorganisms. Therefore, the production of hyaluronic acid is possible from the fermentation of bacteria which produce it naturally. In addition to this, it should be noted that its production is also possible through other genetically modified bacteria.

In the same way that certain bacteria produce hyaluronic acid, there are also bacteria which can produce other sugar or exopolysaccharide polymers. The existence of exopolysaccharides has been known since the 1970s, they are produced by species of bacteria which live in ecosystems known for their extreme conditions. The production of exopolysaccharides by the bacteria which live in these ecosystems is principally related to functions of survival (Raguénès et al. *J Appl Microbiol.*, 1997 April, 82(4):422-30).

Different exopolysaccharides described in the prior art which have been used for cosmetic and/or dermopharmaceutical purposes, such as the exopolysaccharide produced by a strain of bacteria of the genus *Pseudomonas* described in patent EP0534855 B1 which is used as a thickening, gelling and/or texturizing agent. Besides, the patent application FR2871476A1 describes the GY785 strain of hydrothermal origin of the genus *Alteromonas* which produces an exopolysaccharide that can be used as a healing agent; patent EP0987010B1 describes an exopolysaccharide produced by a mesophilic bacterium of hydrothermal origin which improves the skin's defense system and patent application US2010/009931 describes the exopolysaccharide produced by a microalgae strain of the genus *Porphyridium* as a tensing agent, also improving the firmness, elasticity and tonicity of the skin. The American patent application US2009/069213A1 also describes the microalgae strain *Porphyridium* sp. that produces a polysaccharide which presents anti-wrinkle and hydrating properties. U.S. Pat. No. 6,344,346B1 also describes cosmetic compositions with hydrating properties caused by a polysaccharide of natural origin excreted by a bacterium of the genus *Rhizobium*.

Another exopolysaccharide which has proven to have numerous advantageous properties for the skin is the exopolysaccharide described in application WO2009/127057, produced by strains of the bacterial species *Staphylococcus epidermidis* and *Staphylococcus aureus*. After applying a cosmetic composition of this exopolysaccharide the hydration and the morphology of the corneum extract improves, and the desquamation of the skin occurs.

Finally, patent application JP2003-313131 should also be mentioned since it describes a polysaccharide sulfate produced by a strain of *Alteromonas* sp. SN-1009 (FERM BP-5747) with anti-wrinkle properties.

Surprisingly the applicant of this invention has found a new alternative to the exopolysaccharides described in the prior art based on a new exopolysaccharide excreted by the non-hydrothermal bacterial strain *Pseudoalteromonas* sp., deposited with the CNCM under number I-4150 according to the Budapest Treaty, which improves the hydration of the skin, mucous membranes, hair and/or nails and prevents and/or reduces wrinkles.

BRIEF DESCRIPTION

In one aspect of the exemplary embodiment, a method of treatment or care of skin, mucous membranes, hair and/or nails includes administering a cosmetically and/or dermopharmaceutically effective quantity of exopolysaccharide, isolated from the strain of *Pseudoalteromonas* sp. with deposit number CNCM I-4150, to at least one of skin, mucous membranes, hair and nails.

In another aspect of the exemplary embodiment, a process is provided for preparing a composition which includes exopolysaccharide. The method includes fermenting bacterial strain CNCM I-4150 of *Pseudoalteromonas* sp, isolating exopolysaccharide therefrom, and combining the isolated exopolysaccharide with at least one of the group consisting of a cosmetically or dermopharmaceutically acceptable excipient, a cosmetically or dermopharmaceutically acceptable adjuvant, and a cosmetically or dermopharmaceutically acceptable ingredient.

In another aspect of the exemplary embodiment, a cosmetic or dermopharmaceutical composition includes an effective cosmetic or dermopharmaceutical quantity of an exopolysaccharide, isolated from the strain of *Pseudoalteromonas* sp. with deposit number CNCM I-4150, and at least one of the group consisting of a cosmetically or dermopharmaceutically acceptable excipient, a cosmetically or dermopharmaceutically acceptable adjuvant, and a cosmetically or dermopharmaceutically acceptable ingredient.

DESCRIPTION OF THE FIGURES

FIG. 1 shows a comparative study of water retention between the exopolysaccharide of this invention and hyaluronic acid using the dynamic vapor sorption technique.

DETAILED DESCRIPTION OF THE INVENTION

This invention relates to the cosmetic and/or dermopharmaceutical use of the exopolysaccharide excreted by the bacterial strain CNCM I-4150 of the *Pseudoalteromonas* sp species. Surprisingly the inventors of this invention have found that the aforementioned exopolysaccharide is an alternative to hyaluronic acid which solves the problems caused by the lack of hydration of the skin, mucous membranes, hair and/or nails and evens out the skins surface.

Definitions

In order to facilitate the comprehension of this invention, the meanings of some terms and expressions as used in the context of the invention are included.

In the context of this invention "skin" is understood to be the layers which comprise it, from the uppermost layer or stratum corneum to the lowermost layer or hypodermis, both inclusive. These layers are composed of different types of cells such as keratinocytes, fibroblasts, melanocytes and/or adipocytes among others. In the context of this invention, the term "skin" includes the scalp.

In the context of this invention "care of the skin, mucous membranes, hair and/or nails" comprises the prevention of disorders and/or diseases of the skin, mucous membranes, hair and/or nails.

In the context of this invention, the term "aging" refers to the changes experienced by the skin with age (chronoaging) or through exposure to the sun (photoaging) or to environmental agents such as tobacco smoke, extreme climatic conditions of cold, heat, or wind, chemical contaminants or pollutants, and includes all the external visible and/or perceptible changes through touch, such as and not restricted to, the development of discontinuities on the skin such as wrinkles, fine lines, furrows, irregularities or roughness, increase in the size of pores, loss of elasticity, loss of firmness, loss of smoothness, loss of the capacity to recover from deformation, sagging of the skin such as sagging cheeks, the appearance of bags under the eyes or the appearance of a double chin, among others, changes to the color of the skin such as marks, reddening, bags under the eyes or the appearance of hyperpigmented areas such as age spots or freckles among others, anomalous differentiation, hyperkeratinization, elastosis, keratosis, hair loss, orange-peel skin, loss of collagen structure and other histological changes of the stratum corneum, of the dermis, epidermis, vascular system (for example the appearance of spider veins or telangiectasias) or of those tissues close to the skin, among others. The term "photoaging" groups together the set of processes due to the prolonged exposure of the skin to ultraviolet radiation which result in the premature aging of the skin, and present the same physical characteristics as aging, such as and not restricted to, flaccidity, sagging, changes to the color or irregularities in the pigmentation, abnormal and/or excessive keratinization.

The strain which produces the exopolysaccharide in this invention was deposited in accordance with the Budapest Treaty, on Sep. 4, 2009, in the "Collection Nationale de Culture de Microorganismes" [National Microorganism Culture Collection] (CNCM), Pasteur Institute, 28 rue du Docteur Roux, 75724 Paris, France, under code CNCM I-4150.

Thus, a first aspect of this invention relates to the exopolysaccharide of bacterial strain CNCM I-4150 of *Pseudoalteromonas* sp. for the treatment and/or care of the skin, mucous membranes, hair and/or nails.

In a particular embodiment the treatment and/or care of the skin, mucous membranes, hair and/or nails is a treatment and/or prevention of aging. Preferably, the treatment and/or prevention of aging is a treatment and/or prevention of wrinkles on the skin and/or dryness of the skin.

In another particular embodiment the treatment and/or care of the skin, mucous membranes, hair and/or nails is a treatment and/or care of conditions, disorders and/or diseases which are a result of the lack or decrease in hydration of the skin, mucous membranes, hair and/or nails. Preferably the conditions, disorders and/or diseases are selected from the group formed by dry skin, xerosis, hyperkeratosis, reactive hyperkeratosis, palmar and plantar hyperkeratosis, corns and calluses, actinic keratosis, non-actinic keratosis, atopic dermatitis, contact eczema, seborrheic dermatitis, dandruff, cradle cap on babies, acne, rosacea, nevus, ichthyosis, psoriasis, parakeratosis, pityriasis, lichen planus, palmoplantar keratoderma, chapped lips, vaginal dryness, ocular dryness, dry hair, brittle hair and nails.

In another particular embodiment, the treatment and/or care of the skin, mucous membranes, hair and/or nails is carried out by topical, transdermal, oral or parenteral application of the exopolysaccharide of the invention. In the context of this invention, the term "parenteral" includes nasal, auricular, ophthalmic, rectal, urethral, vaginal routes, subcutaneous, intradermal, intravascular injections, such as intravenous, intramuscular, intraocular, intravitreous, intracorneal, intraspinal, intramedullary, intracranial, intracervical, intracerebral, intrameningeal, intraarticular, intrahepatic, intrathoracic, intratracheal, intrathecal and intraperitoneal injections, as well as any another similar injection or infusion technique.

In another particular embodiment, the exopolysaccharide can be obtained through fermentation of the strain of *Pseudoalteromonas* sp. CNCM I-4150 in a suitable culture medium, conventionally stirred and aired to synthesize and secrete the exopolysaccharide into the culture medium. Fermentation to produce the exopolysaccharide of this invention can be carried out in a medium stirred and aerated at a temperature between 20° C. and 32° C., preferably at 29° C., the medium having a pH between 6.5 and 9, preferably around 7.5, adjusting it if necessary during fermentation. The duration of the fermentation is between 30 to 120 hours, preferably between 48 and 96 hours.

In a particular embodiment, in the fermentation of the bacterial strain of *Pseudoalteromonas* sp. of the invention it can be used exogenous sugars as a source of carbon such as and not restricted to, galactose, glucose, mannose, amygdalin, cellobiose, maltose, starch, glycogen, lactose, mixtures thereof and/or extracts containing mixtures of these sugars. In particular, an exogenous supply of glucose of 2 to 40 g/L is provided, preferably from 15 to 25 g/L. Sugar incorporation methods to produce different polysaccharides are described in the prior art, for example and not restricted to, in documents: WO 98/38327, Raguénès et al. *Int. J. Syst. Bact.*, 1997, 47:989-995 and Rougeaux et al., *Carbohidratos. Res.*, 1999, 322:40-45.

In another particular embodiment, mineral salts are provided for the fermentation culture of the bacterial strain CNCM I-4150 of the species *Pseudoalteromonas* sp. For example and not restricted to, they are selected from among salts which provide the ions $Na^+$, $K^+$, $NH_4^+$, $Ca^{2+}$, $Mg^{2+}$, $PO_4^{3-}$, $SO_4^{2-}$, $Cl^-$, $CO_3^{2-}$, or oligo elements such as Cu, Mn, Fe or Zn.

In another particular embodiment, the method of isolation and purification of the exopolysaccharide is carried out by the methods known by the person skilled in the art such as, centrifugation, filtration, ultrafiltration and dialysis. Preferably ultrafiltration and dialysis are carried out with a polyethersulfone membrane which retains molecules of a molecular weight greater than 100,000 Da.

In a particular embodiment, this invention relates to the native exopolysaccharide as well as to any chemical modification known by the person skilled in the art such as sulfation, methylation and/or acetylation, or the formation of exopolysaccharide-metal complexes.

In a preferred embodiment, the molecular weight of the polysaccharide is modified by radical depolymerization resulting in a polymer with a molecular weight comprised between 100 and 800,000 Daltons, preferably a molecular weight of between 100 and 500,000 Daltons, and more preferably a molecular weight of between 100 and 100,000 Daltons. Depolymerization methods are known in the prior art, for example and not restricted to those described in Volpi et al. *Anal. Biochem.*, 1992, 200:100-107.

In a preferred embodiment, the exopolysaccharide excreted by the bacterial strain of the species of *Pseudoalteromonas* sp. CNCM I-4150 is characterized by producing at least four different neutral monosaccharides and two acid monosaccharides. The neutral monosaccharides are preferably mannose, glucose, galactose and N-acetylglucosamine. The acid monosaccharides are preferably glucuronic acid and galacturonic acid. More preferably, the exopolysaccharide of this invention produces a composition in weight of 3% to 12% of mannose, 12% to 34% of glucose, 12% to 34% of glucuronic acid, 2% to 20% of galacturonic acid, 12% to 34% of galactose and 2% to 18% of N-acetylglucosamine, with the condition that the sum of the percentages does not exceed 100%. Even more preferably, the exopolysaccharide produces a composition in weight of 4% to 10% of mannose, 17% to 29% of glucose, 17% to 29% of glucuronic acid, 4% to 18% of galacturonic acid, 17% to 29% of galactose and 4% to 14% of N-acetylglucosamine. Even more preferably, the exopolysaccharide produces a composition in weight of 5% to 9% of mannose, 20% to 26% of glucose, 20% to 26% of glucuronic acid, 9% to 15% of galacturonic acid, 20% to 26% of galactose and 7% to 12% of N-acetylglucosamine. Optionally the exopolysaccharide in addition contains rhamnose.

A second aspect of this invention relates to a cosmetic or dermopharmaceutical composition characterized in that it comprises a cosmetically or dermopharmaceutically effective quantity of the exopolysaccharide of this invention and at least one excipient, adjuvant and/or cosmetically and/or dermopharmaceutically acceptable ingredient.

The cosmetically or dermopharmaceutically effective quantity of the exopolysaccharide in the composition of the invention to be administered, as well as its dosage, will depend on numerous factors, including age, condition of the patient, the nature or severity of the condition, disorder or disease to be treated and/or cared for, the route and frequency of administration and the nature, in particular, of the exopolysaccharides to be used.

"Cosmetically or dermopharmaceutically effective" is understood to be a non-toxic but sufficient quantity of the exopolysaccharide to provide the desired effect. The exopolysaccharide of the invention is used in the cosmetic or dermopharmaceutical composition of this invention at cosmetically or dermopharmaceutically effective concentrations to achieve the desired effect; preferably, with regards to the total weight of the composition, between 0.00000001% (in weight) and 20% (in weight); preferably between 0.000001% (in weight) and 20% (in weight), more preferably between 0.0001% (in weight) and 10% (in weight) and even more preferably between 0.0001% (in weight) and 5% (in weight).

In a particular embodiment, the exopolysaccharide of the invention can also be incorporated into cosmetic and/or dermopharmaceutical delivery systems and/or sustained release systems.

The term "delivery systems" relates to a cosmetically and/or dermopharmaceutically acceptable carrier such as a diluent, adjuvant, excipient, vehicle or additives with which the exopolysaccharide of the invention is administered. These delivery systems are well known in the prior art and can be used for, example, to improve the definitive formulation with regards to organoleptic properties, penetration of the skin and the bioavailability of the active ingredient. These cosmetic and/or dermopharmaceutical vehicles can be liquids, such as water, oils or surfactants, including those of petroleum, animal, plant or synthetic origin, such as and not restricted to, peanut oil, soybean oil, mineral oil, sesame oil, castor oil, polysorbates, sorbitan esters, ether sulfates, sulfates, betaines, glycosides, maltosides, fatty alcohols, nonoxynols, poloxamers, polyoxyethylenes, polyethylene glycols, dextrose, glycerol, digitonin and similar.

The term "sustained release" is used in a conventional sense relating to a delivery system of a compound which provides the gradual release of this compound during a period of time and preferably, although not necessarily, with relatively constant compound release levels over a period of time.

Examples of delivery or sustained release systems are liposomes, mixed liposomes, oleosomes, niosomes, ethosomes, milliparticles, microparticles, nanoparticles and solid lipid nanoparticles, nanostructured lipid supports, sponges, cyclodextrins, vesicles, micelles, mixed micelles of surfactants, surfactant-phospholipid mixed micelles, millispheres, microspheres and nanospheres, liposcheres, millicapsules, microcapsules and nanocapsules, as well as microemulsions and nanoemulsions, which can be added to achieve a greater penetration of the active principle and/or improve its pharmacokinetic and pharmacodynamic properties. Preferred delivery or sustained release systems are liposomes, surfactant-phospholipid mixed micelles and microemulsions, more preferably water-in-oil microemulsions with an internal reverse micelle structure.

The sustained release systems can be prepared by methods known in the prior art, and the compositions which contain them can be administered, for example, by topical or transdermal administration, including adhesive patches, non-adhesive patches, occlusive patches and microelectric patches, or by systemic administration, such as and not restricted to, orally or parenterally, including nasal, rectal or subcutaneous implantation or injection, or direct implantation or injection into a specific body part, and preferably should release a relatively constant quantity of the exopolysaccharide of the invention. The amount of exopolysaccharide contained in the sustained release system will depend, for example, on where the composition is to be administered, the kinetics and duration of the release of the exopolysaccharide of the invention, as well as the nature of the condition, disorder and/or disease to be treated and/or cared for.

The composition containing the exopolysaccharide of this invention can also be adsorbed on solid organic polymers or solid mineral supports, such as and not restricted to, talc, bentonite, silica, starch or maltodextrin among others.

The compositions containing the exopolysaccharide of the invention can also be incorporated into fabrics, nonwoven fabrics or medical devices which are in direct contact with the skin, thus freeing the exopolysaccharide of the invention whether by biodegradation of the binding system to the fabric, non-woven fabric or medical device, or due to the friction between them and the body, due to body moisture, the skin's pH or body temperature. Furthermore, the fabrics and non-woven fabrics can be used for making garments that are in direct contact with the body.

Examples of fabrics, non-woven fabrics, garments, medical devices and means for immobilizing the exopolysaccharide to them, among which are the delivery systems and/or the sustained release systems described above, can be found in literature and are known in the prior art (Schaab C. K. 1986 "Impregnating Fabrics With Microcapsules", HAPPI May 1986; Nelson G. Int. J. Pharm. 2002, 242:55-62; Hipler U. C. y Elsner P. 2006, "Biofunctional Textiles and the Skin", Curr. ProbL Dermatol. v.33, eds. S. Karger AG, Basel, Switzerland; Malcom R. K. et al. J. Cont. Release, 2004, 97:313-320). The preferred fabrics, non-woven fabrics, garments and medical devices are bandages, gauzes, t-shirts, socks, tights, underwear, girdles, gloves, diapers, sanitary napkins, dressings, bedspreads, flannels, adhesive patches, non-adhesive patches, occlusive patches, microelectric patches and/or face masks.

The cosmetic or dermopharmaceutical compositions containing the exopolysaccharide of this invention can be used in different types of compositions of topical or transdermal application, optionally including cosmetically and/or dermopharmaceutically acceptable excipients necessary for formulating the desired administration form.

Compositions of topical or transdermal application can be produced in any solid, liquid or semisolid formulation. Thus, these compositions of topical or transdermal application are, for example and not restricted to, creams, multiple emulsions, such as and not restricted to, oil and/or silicone in water emulsions, water-in-oil and/or silicone emulsions, water/oil/water or water/silicone/water type emulsions, and oil/water/oil or silicone/water/silicone type emulsions, microemulsions, emulsions and/or solutions, liquid crystals, anhydrous compositions, aqueous dispersions, oils, milks, balsams, foams, aqueous or oily lotions, aqueous or oily gels, cream, hydroalcoholic solutions, hydroglycolic solutions, hydrogels, liniments, sera, soaps, shampoos, conditioners, face masks, hairsprays, serums, polysaccharide films, ointments, mousses, pomades, pastes, powders, bars, pencils and sprays or aerosols (sprays), including leave-on and rinse-off formulations. These formulations are topically or transdermally applied on local areas of the skin, mucous membranes, hair and/or nails and can be incorporated using techniques known by the person skilled in the art into different types of solid accessories, such as and not restricted to, bandages, gauzes, t-shirts, socks, tights, underwear, girdles, gloves, diapers, sanitary napkins, dressings, bedspreads, flannels, adhesive patches, non-adhesive patches, occlusive patches, microelectric patches and/or face masks, or they can be incorporated into different make-up products such as make-up foundation, such as fluid foundations and compact foundations, lotions or make-up removers, make-up removal milks, under-eye concealers, eye shadows, lipsticks, lip protectors, lip gloss and powders among others.

The cosmetic or dermopharmaceutical compositions of the invention may include agents which increase the percutaneous absorption of the exopolysaccharide of this invention, for example and not restricted to, dimethyl sulfoxide, dimethylacetamide, dimethylformamide, surfactants, azone (1-dodecylazacycloheptane-2-one), alcohol, urea, ethoxydiglycol, acetone, propylene glycol or polyethylene glycol, among others. Furthermore, the cosmetic or dermopharmaceutical compositions of this invention can be applied to local areas to be treated by means of iontophoresis, sonophoresis, electroporation, microelectric patches, mechanical pressure, osmotic pressure gradient, occlusive cure, microinjections or needle-free injections by means of pressure, such as injections by oxygen pressure, or any combination thereof, to achieve a greater penetration of the exopolysaccharide of the invention. The application area will be determined by the nature of the condition, disorder and/or disease to be treated and/or cared for.

Furthermore, the cosmetic or dermopharmaceutical compositions containing the exopolysaccharide of this invention can be used in different types of formulations for oral administration, preferably in the form of oral cosmetics or medication, such as and not restricted to, capsules, including gelatin capsules, soft capsules, hard capsules, tablets, including sugar coated tablets, powders, granules, chewing gum, solutions, suspensions, emulsions, syrups, polysaccharide films, jellies or gelatins, and any other form known by the person skilled in the art. In particular, the exopolysaccharide of the invention can be incorporated into any form of functional food or fortified food, such as and not restricted to, dietary bars or compact or non-compact powders. These powders can be dissolved in water, soda, dairy products, soya derivatives or can be incorporated into dietary bars. The exopolysaccharide of this invention can be formulated with common excipients and adjuvants for oral compositions or food supplements, such as and not restricted to, fat components, aqueous components, humectants, preservatives, texturizing agents, flavors, aromas, antioxidants and dyes common in the food industry.

The cosmetic or dermopharmaceutical compositions containing the exopolysaccharide of the invention can also be administered by topical or transdermal route, as well as by any other appropriate route, for example oral or parenteral route, for which they will include the pharmaceutically acceptable excipients necessary for the formulation of the desired administration of the exopolysaccharide.

Among the cosmetically or dermopharmaceutically acceptable excipients, adjuvants and/or ingredients contained in the cosmetically or dermopharmaceutically acceptable compositions described in this invention are additional ingredients commonly used in compositions for the treatment and/or care of the skin, mucous membranes, hair and/or nails such as and not restricted to, agents inhibiting acetylcholine receptor clustering, muscle contraction inhibiting agents, anticholinergic agents, elastase inhibiting agents, matrix metalloprotease inhibiting agents, melanin synthesis stimulating or inhibiting agents, whitening or depigmenting agents, propigmenting agents, self-tanning agents, antiaging agents, NO-synthase inhibiting agents, 5α-reductase inhibiting agents, lysyl- and/or prolyl hydroxylase inhibiting agents, antioxidants, free radical scavengers and/or agents against atmospheric pollution, reactive carbonyl species scavengers, anti-glycation agents, antihistamine agents, antiviral agents, antiparasitic agents, emulsifiers, emollients, organic solvents, liquid propellants, skin conditioners such as humectants, substances that retain moisture, alpha hydroxyacids, beta hydroxyacids, moisturizers, epidermal hydrolytic enzymes, vitamins, amino acids, proteins, pigments or colorants, dyes, gelling polymers, thickeners, surfactants, softening agents, anti-wrinkle/anti-aging agents, agents able to reduce or treat bags under the eyes, exfoliating agents, desquamating agents, keratolytic agents, antimicrobial agents, antifungal agents, fungistatic agents, bactericidal agents, bacteriostatic agents, agents stimulating the synthesis of dermal or epidermal macromolecules and/or capable of inhibiting or preventing their degradation, such as for example collagen synthesis-stimulating agents, elastin synthesis-stimulating agents, decorin synthesis-stimulating agents, laminin synthesis-stimulating agents, defensin synthesis-stimulating agents, aquaporin synthesis-stimulation agents, hyaluronic acid synthesis-stimulating agents, fibronectin synthesis-stimulating agents, sirtuin synthesis-stimulating agents, chaperone synthesis-stimulating agents, agents stimulating the synthesis of lipids and components of the stratum corneum (ceramides, fatty acids, etc.), agents that inhibit collagen degradation, agents that inhibit elastin degradation, agents that inhibit serine proteases such as cathepsin G, agents stimulating fibroblast proliferation, agents stimulating keratinocyte proliferation, agents stimulating adipocyte proliferation, agents stimulating melanocyte proliferation, agents stimulating keratinocyte differentiation, agents stimulating adipocyte differentiation, agents that inhibit acetylcholinesterase, skin relaxant agents, glycosaminoglycan synthesis-stimulating agents, anti-hyperkeratosis agents, comedolytic agents, anti-psoriasis agents, DNA repairing agents, DNA protecting agents, stabilizers, anti-itching agents, agents for the treatment and/or care of sensitive skin, firming agents, redensifying agents, restructuring agents, anti-stretch mark agents, binding agents, agents regulating sebum production, lipolytic agents or agents stimulating lipolysis, anti-cellulite agents, antiperspirant agents, agents stimulating healing, coadjuvant healing agents, agents stimulating reepithelialization, coadjuvant reepithelialization agents, cytokine growth factors, calming agents, anti-inflammatory agents and/or analgesics, anesthetic agents, agents acting on capillary circulation and/or microcirculation, agents stimulating angiogenesis, agents that inhibit vascular permeability, venotonic agents, agents acting on cell metabolism, agents to improve dermal-epidermal junction, agents inducing hair growth, hair growth inhibiting or retardant agents, agents delaying hair loss, preservatives, perfumes, chelating agents, vegetable extracts, essential oils, marine extracts, agents obtained from a biofermentation process, mineral salts, cell extracts and sunscreens (organic or mineral photoprotective agents active against ultraviolet A and/or B rays) among others, provided they are physically and chemically compatible with the other components of the composition and in particular with the exopolysaccharide contained in the composition of this invention. Furthermore, the nature of these additional ingredients should not unacceptably alter the benefits of the exopolysaccharide of this invention. The nature of these additional ingredients can be synthetic or natural, such as vegetable extracts, or obtained by a biofermentation process or from a combination of a synthetic process and a biotechnological process. Additional examples can be found in the *CTFA International Cosmetic Ingredient Dictionary & Handbook,* 12th Edition (2008). In the context of this invention, biotechnological process is understood to be any process which produces the active ingredient, or part of it, in an organism, or in one part of it.

In a particular embodiment, the anti-wrinkle and/or anti-aging agent is selected, for example and not restricted to, from the group formed by extracts of *Vitis vinifera, Rosa canina, Curcuma longa, Iris pallida, Theobroma cacao, Ginkgo biloba, Leontopodium Alpinum* or *Dunaliella sauna,* Matrixyl® [INCI: Palmitoyl Pentapeptide-4], Matrixyl 3000® [INCI: Palmitoyl Tetrapeptide-7, Palmitoyl Oligopeptide], Essenskin™ [INCI: Calcium Hydroxymethionine], Renovage [INCI: Teprenone] or Dermaxyl® [INCI: Palmitoyl Oligopeptide] marketed by Sederma/Croda, Vialox® [INCI: Pentapeptide-3], Syn®-Ake® [INCI: Dipeptide Diaminobutyroyl Benzylamide Diacetate], Syn®-Coll [INCI: Palmitoyl Tripeptide-5], Phytaluronate [INCI: Locust Bean (*Ceratonia Siliqua*) Gum] or Preregen® [INCI: *Glycine Soja* (Soybean) Protein, Oxido Reductases] marketed by Pentapharm/DSM, Myoxinol™ [INCI: Hydrolyzed *Hibiscus Esculentus* Extract], Syniorage™ [INCI: Acetyl Tetrapeptide-11], Dermican™ [INCI: Acetyl Tetrapeptide-9] or DN-AGE™ LS [INCI: *Cassia Alata* Leaf Extract] marketed by Laboratoires Sérobiologiques/Cognis, Algisum C® [INCI: Methylsilanol Mannuronate] or Hydroxyprolisilane CN® [INCI: Methylsilanol Hydroxyproline Aspartate] marketed by Exsymol, Argireline® [INCI: Acetyl Hexapeptide-8], SNAP-7 [INCI: Acetyl Heptapeptide-4], SNAP-8 [INCI: Acetyl Octapeptide-3], Leuphasyl® [INCI: Pentapeptide-18], Aldenine® [INCI: Hydrolized Wheat Protein, Hydrolized Soy Protein, Tripeptide-1], Preventhelia® [INCI: Diaminopropionoyl Tripeptide-33], Decorinyl™ [INCI: Tripeptide-10 Citrulline], Trylagen® [INCI: *Pseudoalteromonas* Ferment Extract, Hydrolyzed Wheat Protein, Hydrolyzed Soy Protein, Tripeptide-10 Citrulline, Tripeptide-1], Eyeseryl® [INCI: Acetyl Tetrapeptide-5], Peptide AC29 [INCI: Acetyl Tripeptide-30 Citrulline], Lipochroman-6 [INCI: Dimethylmethoxy Chromanol], Chromabright™ [INCI: Dimethylmethoxy Chromanyl Palmitate], Serilesine® [INCI: Hexapeptide-10], Antarcticine® [INCI: *Pseudoalteromonas* Ferment Extract], Vilastene™ [INCI: Lysine HCl, Lecithin, Tripeptide-10 Citrulline], dGlyage™ [INCI: Lysine HCl, Lecithin, Tripeptide-9 Citrulline], Relistase™ [INCI: Acetylarginyltriptophyl Diphenylglycine], Thermostressine™ [INCI: Acetyl Tetrapeptide-22] or Inyline™ [INCI: Acetyl Hexapeptide-30] marketed by Lipotec, Kollaren® [INCI: Tripeptide-1, Dextran] marketed by Institut Europeen de Biologie Cellulaire/Unipex, Collaxyl® IS [INCI: Hexapeptide-9], Laminixyl IS™ [INCI: Heptapeptide], Orsirtine™ GL [INCI: *Oryza Sativa* (Rice) Extract], D'Orientine™ IS [INCI: *Phoenix Dactylifera* (Date) Seed Extract], Phytoquintescine™ [INCI: Einkorn (*Triticum Monococcum*) Extract] or Quintescine™ IS [INCI: Dipeptide-4] marketed by Vincience/ISP, BONT-L-Peptide [INCI: Palmitoyl Hexapeptide-19] marketed by *Infinitec Activos*, Deepaline™ PVB [INCI: Palmitoyl Hydrolyzed Wheat Protein] or Sepilift® DPHP [INCI: Dipalmitoyl Hydroxyproline] marketed by Seppic, Gatuline® Expression [INCI: *Acmella Oleracea* Extract], Gatuline® In-Tense [INCI: *Spilanthes Acmella* Flower Extract] or Gatuline® Age Defense 2 [INCI: *Juglans Regia* (Walnut) Seed Extract] marketed by Gattefossé, Thalassine™ [INCI: *Algae* Extract] marketed by Biotechmarine, ChroNOline™ [INCI: Caprooyl Tetrapeptide-3] or Thymulen-4 [INCI: Acetyl Tetrapeptide-2] marketed by Atrium Innovations/Unipex Innovations, EquiStat [INCI: *Pyrus Malus* Fruit Extract, *Glycine Soja* Seed Extract] or Juvenesce [INCI: Ethoxydiglicol and Caprylic Triglycerid, Retinol, Ursolic Acid, Phytonadione, Ilomastat] marketed by Coletica/Engelhard/BASF, Ameliox [INCI: Carnosine, Tocopherol, *Silybum Marianum* Fruit Extract] or PhytoCellTec *Malus Domestica* [INCI: *Malus Domestica* Fruit Cell Culture] marketed by Mibelle Biochemistry, Bioxilift [INCI: *Pimpinella Anisum* Extract] or SMS Anti-Wrinkle® [INCI: *Annona Squamosa* Seed Extract] marketed by Silab, antagonists of the $Ca^{2+}$ channel such as and not restricted to, alverine, manganese or magnesium salts, certain secondary or tertiary amines, retinol and its derivatives, resveratrol, idebenone, coenzyme Q10 and its derivatives, boswellic acid and its derivatives, GHK and its derivatives and/or salts, carnosine and its derivatives, DNA repairing enzymes such as and not restricted to, photolyase or T4 endonuclease V, or chloride channel agonists, among others.

In a particular embodiment, the humectant or moisture retaining substance, moisturizer or emollient is selected, for example and not restricted to, from the group formed by polyols and polyethers such as glycerin, ethylhexylglycerin, caprylyl glycol, pentylene glycol, butylene glycol, propylene glycol and its derivatives, triethylene glycol, polyethylene glycol, Glycereth-26, Sorbeth-30; panthenol; pyroglutamic acid and its salts and derivatives; amino acids, such as serine, proline, alanine, glutamate or arginine; ectoin and its derivatives; N-(2-hydroxyethyl)acetamide; N-lauryl-pyrrolidone carboxylic acid; N-lauryl-L-lysine; N-alpha-benzoyl-L-arginine; urea; creatine; α- and β-hydroxyacids such as lactic acid, glycolic acid, malic acid, citric acid or salicylic acid, and their salts; polyglyceryl acrylate; sugars and polysaccharides, such as glucose, saccharide isomerate, sorbitol, pentaerythritol, inositol, xylitol, trehalose and their derivatives, sodium glucuronate, carraghenates (*Chondrus crispus*) or chitosan; glycosaminoglycans such as hyaluronic acid and its derivatives; aloe vera in any of its forms; honey; soluble collagen; lecithin and phosphatidylcholine; ceramides; cholesterol and its esters; tocopherol and its esters, such as tocopheryl acetate or tocopheryl linoleate; long chain alcohols such as cetearyl alcohol, stearyl alcohol, cetyl alcohol, oleyl alcohol, isocetyl alcohol or octadecan-2-ol; long chain alcohol esters such as lauryl lactate, myristyl lactate or $C_{12}$-$C_{15}$ alkyl benzoate; fatty acids such as stearic acid, isostearic acid or palmitic acid; polyunsaturated fatty acids (PUFAs); sorbitans such as sorbitan distearate; glycerides such as glyceryl monoricinoleate, glyceryl monostearate, glyceryl stearate citrate or caprylic acid and capric acid triglyceride; saccharose esters such as saccharose palmitate or saccharose oleate; butylene glycol esters, such as dicaprylate and dicaprate; fatty acids such as isopropyl isostearate, isobutyl palmitate, isocetyl stearate, isopropyl laurate, hexyl laurate, decyl oleate, cetyl palmitate, di-n-butyl sebacate, isopropyl myristate, isopropyl palmitate, isopropyl stearate, butyl stearate, butyl myristate, isopropyl linoleate, 2-ethylhexyl palmitate, 2-ethylhexyl cocoate, decyl oleate, myristyl myristate; squalene; squalane; mink oil; lanolin and its derivatives; acetylated lanolin alcohols; silicon derivatives such as cyclomethicone, dimethicone or dimethylpolysiloxane; Antarcticine® [INCI: *Pseudoalteromonas* Ferment Extract], Xpertmoist™ [INCI: Glycerin, *Pseudoalteromonas* Ferment Extract, Xanthan Gum, Proline, Alanine, Serine, Ethylhexylglycerin, Caprylyl Glycol] or Bodyfensine™ [INCI: Acetyl Dipeptide-3 Aminohexanoate] marketed by Lipotec, petrolatum; mineral oil; mineral and synthetic waxes; beeswax (cera alba); paraffin; or waxes and oils of vegetable origin such as candelilla wax (*Euphorbia cerifera*), carnauba wax (*Copernicia cerifera*), shea butter (*Butirospermum parkii*), cocoa butter (*Theobroma cacao*), castor oil (*Ricinus communis*), sunflower oil (*Helianthus annuus*), olive oil (*Olea europaea*), coconut oil (*Cocos nucifera*), palm oil (*Elaeis guineensis*), wheat germ oil (*Triticum vulgare*), sweet almond oil (*Prunus amygdalus dulces*), musk rose seed oil (*Rosa moschata*), wild soybean oil (*Glycine soja*), grape seed oil (*Vitis vinifera*), calendula oil (*Calendula officinalis*), jojoba oil (*Simmonsis chinensis*), mango oil (*Mangifera indica*), avocado oil (*Persea gratissima*), and/or mixtures thereof, among others.

Furthermore, in another particular embodiment, the agent stimulating healing, coadjuvant healing agent, agent stimulating reepithelialization and/or coadjuvant reepithelialization agent is selected, for example and not restricted to, the group formed by extracts of *Aristoloquia clematis*, *Centella asiatica*, *Rosa moschata*, *Echinacea angustifolia*, *Symphytum officinale*, *Equisetum arvense*, *Hypericum perforatum*, *Mimosa tenuiflora*, *Persea gratisima*, *Prunus africanum*, *Tormentilla erectea*, *Aloe vera*, Polyplant® Epithelizing [INCI: *Calendula Officinalis*, *Hypericum Perforatum*, *Chamomilla Recutita*, *Rosmarinus Officinalis*] marketed by Provital, Cytokinol® LS 9028 [INCI: Hydrolyzed Casein, Hydrolyzed Yeast Protein, Lysine HCl] marketed by Laboratories Serobiologiques/Cognis or Deliner® [INCI: *Zea May* (Corn) Kernel Extract] marketed by Coletica/Engelhard/BASF, allantoin, cadherins, integrins, selectins, hyaluronic acid receptors, immunoglobulins, fibroblast growth factors, connective tissue growth factors, platelet-derived growth factors, vascular endothelial growth factors, epidermal growth factors, insulin-like growth factor, keratinocyte growth factors, colony-stimulating factors, transforming growth factor-beta, tumor necrosis factor-alpha, interferons, interleukins, matrix metalloproteinases, receptor protein tyrosine phosphatases, Antarcticine® [INCI: *Pseudoalteromonas* Ferment Extract], Decorinyl® [INCI: Tripeptide-10 Citrulline], Trylagen® [INCI: *Pseudoalteromonas* Ferment Extract, Hydrolyzed Wheat Protein, Hydrolyzed Soy Protein, Tripeptide-10 Citrulline, Tripeptide-1], Xpertmoist™ [INCI: Glycerin, *Pseudoalteromonas* Ferment Extract, Xanthan Gum, Proline, Alanine, Serine, Ethylhexylglycerin, Caprylyl Glycol] or Bodyfensine™ [INCI: Acetyl Dipeptide-3 Aminohexanoate] marketed by Lipotec, among others.

In a particular embodiment, the agent stimulating the synthesis of dermal or epidermal macromolecules is selected, for example and not restricted to, from the group formed by collagen synthesis-stimulating agent, elastin synthesis-stimulation agent, decorin synthesis-stimulation agent, laminin synthesis-stimulation agent, chaperone synthesis-stimulating agent, sirtuin synthesis-stimulating agent, hyaluronic acid synthesis-stimulating agent, aquaporin synthesis-stimulating agent, fibronectin synthesis-stimulating agent, agents that inhibit collagen degradation, agents that inhibit serine proteases such as leukocyte elastase or cathepsin G, agents stimulating fibroblast proliferation, agents stimulating adipocyte proliferation, agents stimulating adipocyte differentiation, glycosaminoglycan synthesis-stimulating agents, and DNA repairing agents and/or DNA protecting agents, such as and not restricted to extracts of *Centella asiatica*, *Saccharomyces cerevisiae*, *Solanum tuberosum*, *Rosmarinus officinalis*, *Vaccinium angustifolium*, extract of the algae *Macrocystis pyrifera*, *Padina pavonica*, extract of soy, malt, flax, sage, red clover, kakkon, white lupin plants, hazelnut extract, maize extract, yeast extract, beech shoot extracts, leguminous seed extract, plant hormone extract such as gibberellins, auxins or cytokinins, among others, or extract of saline zooplankton, the fermentation product of milk with *Lactobacillus Buigaricus*, asiaticosides and their derivatives, vitamin C and its derivatives, cinnamic acid and its derivatives, Matrixyl® [INCI: Palmitoyl Pentapeptide-3], Matrixyl® 3000 [INCI: Palmitoyl Tetrapeptide-3, Palmitoyl Oligopeptide] or Biopeptide CL™ [INCI: Glyceryl Polymethacrylate, Propylene Glycol, Palmitoyl Oligopeptide] marketed by Sederma/Croda, Antarcticine® [INCI: *Pseudoalteromonas* Ferment Extract], Decorinyl® [INCI: Tripeptide-10 Citrulline], Serilesine® [INCI: Hexapeptide-10], Lipeptide [INCI: Hydrolized Vegetable Protein], Aldenine® [INCI: Hydrolized Wheat Protein, Hydrolized Soy Protein, Tripeptide-1], Relistase™ [INCI: Acetylarginyltryptophyl Diphenylglycine], Thermostressine™ [INCI: Acetyl Tetrapeptide-22] or Peptide AC29 [INCI: Acetyl Tripeptide-30 Citrulline] marketed by Lipotec, Drieline® PF [INCI: Yeast Betaglucan] marketed by Alban Muller, Phytovityl C® [INCI: Aqua, *Zea Mays*

Extract] marketed by Solabia, Collalift® [INCI: Hydrolyzed Malt Extract] marketed by Coletica/Engelhard/BASF, Phytocohesine PSP™ [INCI: Sodium Beta-Sitosterol Sulfate] marketed by Seporga/Vincience/ISP, minerals such as calcium, among others, retinoids and their derivatives, isoflavonoids, carotenoids, in particular lycopene, pseudodipeptides, retinoids and their derivatives such as retinol or retinyl palmitate, among others, or heparinoids, among others.

In a particular embodiment, the agent inhibiting elastin degradation is selected, for example and not restricted to, from the group formed by Elhibin® [INCI: *Glycine Soja* (Soybean) Protein], Preregen® [INCI: *Glycine Soja* (soybean) Protein, Oxido Reductases] or Regu®-Age [INCI: Hydrolyzed Rice Bran Protein, *Glycine Soja* (Soybean) Protein, Oxido Reductases] marketed by Pentapharm/DSM, Juvenesce [INCI: Ethoxydiglicol and Caprylic Triglycerid, Retinol, Ursolic Acid, Phytonadione, Ilomastat], Micromerol™ [INCI: *Pyrus Malus* Extract], Heather Extract [INCI: *Calluna Vulgaris* Extract], Extracellium® [INCI: Hydrolyzed Potato Protein] or Flavagrum™ PEG [INCI: PEG-6 Isostearate, Hesperetin Laurate] marketed by Coletica/Engelhard/BASF, Proteasyl® TP LS8657 [INCI: *Pisum Sativum* Extract] marketed by Laboratoires Sérobiologiques/Cognis, Relistase™ [INCI: Acetylarginyltryptophyl Diphenylglycine] marketed by Lipotec, Sepilift DPHP [INCI: Dipalmitoyl Hydroxyproline] marketed by SEPPIC, Vitaderm® [INCI: Alcohol, Water (Aqua), Glycerin, Hydrolyzed Rice Protein, *Ilex Aquifolium* Extract, Sodium Ursolate, Sodium Oleanolate] marketed by Rahn, Gatuline® Age Defense 2 [INCI: *Juglans Regia* (Walnut) Seed Extract] marketed by Gattefosse, IP 2000 [INCI: Dextran, Trifluoroacetyl Tripeptide-2] marketed by IEB and Atrium Innovations/Unipex Innovations, Radicaptol [INCI: Propylene Glycol, Water (Aqua), *Passiflora Incarnata* Flower Extract, *Ribes Nigrum* (Blackcurrant) Leaf Extract, *Vitis Vinifera* (grape) Leaf Extract] marketed by Solabia or ViaPure™ *Boswellia* [INCI: Olivanum (*Boswellia Serrata*) Extract] marketed by Soliance, among others.

In a particular embodiment, the matrix metalloproteinase inhibitory agent is selected, for example and not restricted to, from the group formed by ursolic acid, isoflavones such as genistein, quercetin, carotenoids, lycopene, soya extract, cranberry extract, rosemary extract, extract of *Trifolium pratense* (red clover), extract of *Phormium tenax* (New Zealand flax), kakkon-to extract, sage extract, retinol and its derivatives, retinoic acid and its derivatives, sapogenins such as diosgenin, hecogenin, smilagenin, sarsapogenin, tigogenin, yamogenin and yucagenin, among others, Collalift® [INCI: Hydrolyzed Malt Extract], Juvenesce [INCI: Ethoxydiglicol and Caprylic Triglyceride, Retinol, Ursolic Acid, Phytonadione, Ilomastat] or EquiStat [INCI: *Pyrus Malus* Fruit Extract, *Glycine Soja* Seed Extract] marketed by Coletica/Engelhard/BASF, Pepha®-Timp [INCI: Human Oligopeptide-20], Regu-Age [INCI: Hydrolyzed Rice Bran Protein, *Glycine Soja* Protein, Oxido Reductases] or Colhibin [INCI: Hydrolyzed Rice Protein] marketed by Pentapharm/DSM, Lipeptide [INCI: Hydrolized Vegetable Protein] or Peptide AC29 [INCI: Acetyl Tripeptide-30 Citrulline] marketed by Lipotec, Litchiderm™ [INCI: Litchi *Chinensis* Pericarp Extract] or Arganyl™ [INCI: *Argania Spinosa* Leaf Extract] marketed by Laboratoires Sérobiologiques/Cognis, MDI Complex® [INCI: Glycosaminoglycans] or ECM-Protect® [INCI: Water (Aqua), Dextran, Tripeptide-2] marketed by Atrium Innovations/Unipex Innovations, Dakaline [INCI: *Prunus Amygdalus* Dulcis, *Anogeissus Leiocarpus* Bark Extract] marketed by Soliance, Homeostatine [INCI: Enteromorpha Compressa, Caesalpinia Spinosa] marketed by Provital, Timp-Peptide [proposed INCI: Acetyl Hexapeptide] or ECM Moduline [proposed INCI: Palmitoyl Tripeptide] marketed by Infinitec Activos, IP2000 [INCI: Dextran, Trifluoroacetyl Tripeptide-2] marketed by Institut Europeen de Biologie Cellulaire/Unipex, Actimp 1.9.3® [INCI: Hydrolyzed Lupine Protein] marketed by Expanscience Laboratories, Vitaderm® [INCI: Alcohol, Water (Aqua), Glycerin, Hydrolyzed Rice Protein, *Hex Aquifolium* Extract, Sodium Ursolate, Sodium Oleanolate] marketed by Rahn, adapalene, tetracyclines and their derivatives such as minocycline, rolitetracycline, chlortetracycline, metacycline, oxytetracycline, doxycycline, demeclocycline and their salts, Batimastat [BB94; [4-(N-hydroxyamino)-2R-isobutyl-3S-(thiophene-2-ilthymethyl)succinyl]-L-phenylalanine-N-methylamide], Marimastat [BB2516; [2S—[N-4(R*),2R*,3S]]-N-4[2,2-dimethyl-1-[methylaminocarbonyl]propyl]-N1,2-dyhydroxy-3-(2-methyl-propyl)butanediamide], among others.

In a particular embodiment, the firming and/or redensifying agent is selected, for example and not restricted to, from the group formed by extracts of *Malpighia punicitolia, Cynara scolymus, Gossypium herbaceum, Aloe Barbadensis, Panicum miliaceum, Morus nigra, Sesamum indicum, Glycine soja, Triticum vulgare*, Pronalen® Refirming HSC [INCI: *Triticum Vulgare, Silybum Marianum, Glycine Soy, Equisetum Arvense, Alchemilla Vulgaris, Medicago Sativa, Raphanus Sativus*] or Polyplant® Refirming [INCI: Coneflower, Asiatic *Centella*, Fucus, Fenugreek] marketed by Provital, Lanablue® [INCI: Sorbitol, *Algae* Extract] marketed by Atrium Innovations/Unipex Innovations, Pepha®-Nutrix [INCI: Natural Nutrition Factor] marketed by Pentapharm/DSM, plant extracts containing isoflavones, Biopeptide EL™ [INCI: Palmitoyl Oligopeptide], Biopeptide CL™ [INCI: Palmitoyl Oligopeptide], Vexel® [INCI: Water (Aqua), Propylene Glycol, Lecithin, Caffeine, Palmitoyl Carnitine], Matrixyl® [INCI: Palmitoyl Pentapeptide-3], Matrixyl® 3000 [INCI: Palmitoyl Tetrapeptide-3, Palmitoyl Oligopeptide] or Bio-Bustyl™ [INCI: Glyceryl Polymethacrylate, *Rahnella* Soy Protein Ferment, Water (Aqua), Propylene Glycol, Glycerin, PEG-8, Palmitoyl Oligopeptide] marketed by Sederma/Croda, Dermosaccharides® HC [INCI: Glycerin, Water (Aqua), Glycosaminoglycans, Glycogen], Aglycal® [INCI: Mannitol, Cyclodextrin, Glycogen, Aratostaphylos *Uva Ursi* Leaf Extract], Cytokinol® LS [INCI: Hydrolyzed Casein, Hydrolyzed Yeast Protein, Lysine HCl] or Firmiderm® LS9120 [INCI: *Terminalia Catappa* Leaf Extract, *Sambucus Negra* Flower Extract, PVP, Tannic Acid] marketed by Laboratoires Serobiologiques/Cognis, Liftline® [INCI: Hydrolyzed Wheat Protein], Raffermine® [INCI: Hydrolyzed Soy Flour] or Ridulisse C® [Hydrolyzed Soy Protein] marketed by Silab, Serilesine® [INCI: Hexapeptide-10], Decorinyl™ [INCI: Tripeptide-10 Citrulline] or Trylagen® [INCI: *Pseudoalteromonas* Ferment Extract, Hydrolyzed Wheat Protein, Hydrolyzed Soy Protein, Tripeptide-10 Citrulline, Tripeptide-1] marketed by Lipotec, Ursolisome® [INCI: Lecithin, Ursolic Acid, Atelocollagen, Xanthan Gum, Sodium Chondroitin Sulfate] or Collalift® [INCI: Hydrolyzed Malt Extract] marketed by Coletica/Engelhard/BASF, Syn®-Coll [INCI: Palmitoyl Tripeptide-5] marketed by Pentapharm/DSM, Hydriame® [INCI: Water (Aqua), Glycosaminoglycans, Sclerotium Gum] marketed by Atrium Innovations/Unipex Innovations or IP2000 [INCI: Dextran, Trifluoroacetyl Tripeptide-2] marketed by Institut Europeen de Biologie Cellulaire/Unipex, among others.

In a particular embodiment, the desquamating agent and/or keratolytic agent and/or exfoliating agent is selected, for example and not restricted to, from the group formed by hydroxyacids and their derivatives, β-hydroxyacids, in particular salicylic acid and its derivatives, or gentisic acid; α-hydroxyacids and its salts, such as glycolic acid, ammonium glycolate, lactic acid, 2-hydroxyoctanoic acid, α-hydroxycaprylic acid, mandelic acid, citric acid, malic acid or tartaric acid; α- and β-hydroxybutyric acids; polyhydroxy acids such as gluconic acid, glucuronic acid or saccharic acid; keto acids such as pyruvic acid, glyoxylic acid; carboxylic pyrrolidine acid; cysteic acid and derivatives; aldobionic acids; azelaic acid and its derivatives such as azeloyl diglycinate; ascorbic acid and its derivatives such as 6-O-palmitoylascorbic acid, ascorbyl glucoside, dipalmitoyl ascorbic acid, magnesium ascorbyl acid-2-phosphate salt (MAP), sodium ascorbyl acid-2-phosphate salt (NAP), ascorbyl tetraisopalmitate (VCIP); nicotinic acid, its esters and nicotinamide (also known as vitamin B3 or vitamin PP); nordihydroguaiaretic acid; urea; oligofucoses; cinnamic acid; derivatives of jasmonic acid; hydroxystilbenes such as resveratrol; extract of *Saccarum officinarum*; enzymes involved in desquamation or degradation of corneodesmosomes, such as glycosidases, stratum corneum chymotryptic enzyme (SCCE) or other proteases such as trypsin, chymotrypsin, sutilain, papain or bromelain; chelating agents such as ethylenediaminetetraacetic acid (EDTA) and its salts, amino sulfide compounds such as 4 (2-hydroxyethyl) piperazine-1-ethanesulfonic acid (HEPES) or methylglycine sodium diacetate (TRILON® M marketed by BASF); derivatives of 2-oxothiazolidine-4-carboxylic acid (procystein); derivatives of sugars such as O-octanoyl-6-D-maltose and N-acetylglucosamine; chestnut extract (*Castanea sativa*) such as that marketed by SILAB under the name Recoverine® [INCI: Water (Aqua), *Castanea Sativa* Seed Extract]; opuntia extract (*Opuntia ficus-indica*) such as that marketed by SILAB such as Exfolactive® [INCI: Hydrolyzed *Opuntia Ficus Indica* Flower Extract]; or Phytosphingosine SLC® [INCI: Salicyloyl Phytosphingosine] marketed by Degussa/Evonik, Peel-Moist [INCI: Glycerin, Papain, Calcium Pantothenate, Xanthan Gum, Caprylyl Glycol, Urea, Magnesium Lactate, Ethylhexylglycerin, Potassium Lactate, Serine, Alanine, Proline, Magnesium Chloride, Sodium Citrate] marketed by Lipotec; extract or combination of extracts of *Saphora japonica*, papaya, pineapple, pumpkin or sweet potato, and/or mixtures thereof.

Applications

A third aspect of this invention refers to the use of the exopolysaccharide of the invention in the preparation of a cosmetic or dermopharmaceutical composition for the treatment and/or care of the skin, mucous membranes, hair and/or nails.

In a particular embodiment, this invention refers to the use of the exopolysaccharide in the preparation of a cosmetic or dermopharmaceutical composition for the treatment and/or prevention of aging. Preferably the treatment and/or prevention of aging is a treatment and/or prevention of wrinkles on the skin and/or dry skin.

In another particular embodiment, this invention refers to the use of the exopolysaccharide in the preparation of a cosmetic or dermopharmaceutical composition for the treatment and/or care of any conditions, disorders and/or diseases which are a result of a lack or decrease in the hydration of the skin, mucous membranes, hair and/or nails. Preferably the conditions, disorders and/or diseases are selected from the group formed by dry skin, xerosis, hyperkeratosis, hyperkeratosis response, palmar and plantar hyperkeratosis, corns and calluses, actinic keratosis, non-actinic keratosis, atopic dermatitis, contact eczema, seborrheic dermatitis, dandruff, cradle cap on babies, acne, rosacea, nevus, ichthyosis, psoriasis, parakeratosis, pityriasis, lichen planus, palmoplantar keratoderma, chapped lips, vaginal dryness, ocular dryness, dry hair, brittle hair and nails.

Examples of cosmetic or dermopharmaceutical compositions for the treatment and/or care of the skin, mucous membranes, hair and/or nails include creams, multiple emulsions, such as and not restricted to, oil and/or silicone in water emulsions, water-in-oil and/or silicone emulsions, water/oil/water or water/silicone/water type emulsions, and oil/water/oil or silicone/water/silicone type emulsions, anhydrous compositions, aqueous dispersions, oils, milks, balsams, foams, lotions, gels, cream gels, hydroalcoholic solutions, hydroglycolic solutions, hydrogels, liniments, sera, soaps, shampoos, conditioners, serums, polysaccharide films, ointments, mousses, pomades, powders, bars, pencils and sprays or aerosols (sprays), including leave-on and rinse-off formulations, bandages, gauzes, t-shirts, socks, tights, underwear, girdles, gloves, diapers, sanitary napkins, dressings, bedspreads, flannels, adhesive patches, non-adhesive patches, occlusive patches, microelectric patches and/or face masks, make-up products such as make-up foundation, such as fluid foundations and compact foundations, make-up removal lotions, make-up removal milks, under-eye concealers, eye shadows, lipsticks, lip protectors, lip gloss and powders among others. The cosmetic or dermopharmaceutical compositions containing the exopolysaccharide of this invention can also be incorporated into products for the treatment, care and/or cleaning of nails and cuticles such as nail varnishes, nail varnish remover and cuticle remover lotions, among others. The compositions containing the exopolysaccharide of this invention can be applied to the skin, mucous membranes, hair and/or nails or can be administered orally or parenterally depending on the requirements to treat and/or care for a condition, disorder and/or disease.

The cosmetic or dermopharmaceutical compositions of this invention can be applied to the skin by means of iontophoresis, sonophoresis, electroporation, microelectric patches, mechanical pressure, osmotic pressure gradient, occlusive cure, microinjections or needle-free injections by means of pressure, such as injections by oxygen pressure, or any combination thereof, to achieve a greater penetration of the exopolysaccharide of the invention.

An additional aspect of this invention refers to a method of treatment and/or care of the skin, mucous membranes, hair and/or nails which comprises the administration of a cosmetically and/or dermopharmaceutically effective quantity of the exopolysaccharide, preferably in the form of a cosmetic or dermopharmaceutical composition containing it.

Another additional aspect of this invention refers to a method for the treatment and/or care of any conditions, disorders and/or diseases of mammals, preferably of humans, which are a consequence of a lack or decrease in the hydration of the skin, mucous membranes, hair and/or nails, which comprises the administration of an effective quantity of the exopolysaccharide, preferably in the form of a cosmetic or dermopharmaceutical composition containing them.

In a preferred embodiment, the conditions, disorders and/or diseases which are a consequence of a lack or decrease in the hydration of the skin, mucous membranes, hair and/or nails are selected from the group formed by dry skin, xerosis, hyperkeratosis, hyperkeratosis response, palmar and plantar hyperkeratosis, corns and calluses, actinic keratosis, non-actinic keratosis, atopic dermatitis, contact eczema, seborrheic dermatitis, dandruff, cradle cap on babies, acne, rosacea, nevus, ichthyosis, psoriasis, parakeratosis, pityriasis, lichen planus, palmoplantar keratoderma, chapped lips, vaginal dryness, ocular dryness, dry hair, brittle hair and nails.

According to an additional aspect, this invention refers to the treatment and/or care which reduces, delays and/or prevents the signs of aging and which comprises the administration of an effective quantity of the exopolysaccharide, preferably in the form of a cosmetic or dermopharmaceutical composition containing it. Preferably the treatment and/or care which reduces, delays and/or prevents the signs of aging is a treatment and/or prevention of wrinkles on the skin and/or dryness of the skin.

In a more particular aspect, the treatment and/or care of this invention is carried out by topical or transdermal application, preferably, the topical or transdermal application is carried out by means of iontophoresis, sonophoresis, electroporation, mechanical pressure, osmotic pressure gradient, occlusive cure, microinjections, with needle-free injections by means of pressure, microelectric patches or any combination thereof.

In another particular aspect, the treatment and/or care is carried out by oral administration.

In another particular aspect, the treatment and/or care is carried out by parenteral application.

The frequency of the application or administration can vary widely, depending on the needs of each subject and severity of the condition, disorder or disease to be treated or cared for, suggesting a range of application or administration from once per month to tenth times per day, preferably from once per week to four times per day, more preferably from three times per week to three times per day, even more preferably once or twice per day.

This invention is understood more clearly with the help of the following examples, without limitation and included for illustrative purposes only which describe the preparation and characterization of exopolysaccharides and compositions containing them in accordance with the invention.

FIG. 1 shows a comparative study of water retention between the exopolysaccharide of this invention and the hyaluronic acid using the dynamic vapor sorption technique.

EXAMPLES

Example 1: Preparation and Isolation of the Exopolysaccharide Secreted by Strain CNCM I-4150 Corresponding to the Species *Pseudoalteromonas* sp a) Method of Cultivation of Strain CNCM I-4150 Corresponding to the Species *Pseudoalteromonas*.

Strain CNCM I-4150 was cultivated in a fermenter, at 29° C. and at a pH of 7.5, whose broth contained 2216E medium (ZoBell C. E. *J. Mar. Res.*, 1941, 4:42.) enriched with glucose (20 g/l). An inoculum was prepared with 10% (v/v) of a previous crop and the duration of the fermentation was extended to 72 hours. The speed of aeration and stirring was 2 vvm and 250 rpm, respectively.

b) Purification of the Exopolysaccharide.

The bacteria were separated from the broth by centrifugation at 12,000 g for 45 mins. The polysaccharide was purified with distilled water by ultrafiltration with a polyethersulfone membrane for polysaccharides of over 100 KDa in molecular weight. Once purified, the polysaccharide was depolymerized by radical depolymerization (Volpi N. et al. *Anal. Biochem.*, 1992, 200:100-107) resulting in a polymer with a molecular weight between 3,000 and 40,000 Da.

Example 2: Physical-Chemical Characterization of the Exopolysaccharide Produced by Bacterial Strain CNCMI-4150 Corresponding to the Species *Pseudoalteromonas* sp.

a) Chemical Analysis

The content of neutral and acid monosaccharides of the exopolysaccharide obtained was determined according to that described in example 1 by hydrolysis and chromatography of gases according to the method described by Kamerling et al. *Biochem. J.*, 1975 151:491-495, and modified by Montreuil et al. in 1986, Glycoproteins. In Carbohydrate analysis: a practical approach. Eds Chaplin et Kennedy, I.R.L Press, Oxford, Washington D.C., pp 143-204. The percentual relationship of sugars obtained was 7.25% of mannose, 24.64% of glucose, 23.19% of glucuronic acid, 11.59% of galacturonic acid, 24.64% of galactose and 8.70% of N-acetylglucosamine.

Example 3: Preparation of a Cosmetic Composition of the Exopolysaccharide Excreted by Bacterial Strain CNCM I-4150

In a suitable vessel the following ingredients were added in this order: water [INCI: Water (Aqua)], Phenonip™ [INCI: Phenoxyethanol, Methylparaben, Ethylparaben, Butylparaben, Propylparaben, Isobutylparaben], Abiol [INCI: Imidazolidinyl Urea] and Propylene Glycol USP/EP [INCI: Propylene Glycol] (phase A ingredients). The mixture of ingredients in phase A was subjected to constant stirring and subsequently Carbopol® ETD 2020 [INCI: Acrylates/C10-30 Alkyl Acrylate Crosspolymer] was added (phase B). The resulting mixture was heated in a microwave to 65° C.

In another vessel Lipomulse 165 [INCI: Glyceryl Stearate, PEG-100 Stearate], Alcohol CO-1695 [INCI: Cetyl Alcohol], Edenor L2SM [INCI: Stearic Acid, Palmitic Acid], Caprylic Capric Triglycerides [INCI: Caprylic/Capric Triglyceride] and Massocare HD [INCI: Isohexadecane] were added (phase C ingredients). Phase C was dissolved in a bath at about 75° C.

In a third vessel the exopolysaccharide obtained according to example 1 in water with sodium salicylate [INCI: Sodium Salicylate] was dissolved (phase D).

Next, the mixture of ingredients from phase C was added to the mixture of ingredients from A and B, under turbine stirring at 75° C. until the emulsion was formed.

Subsequently, when the previous mixture of A, B and C was cooled to 40° C., the dissolution of the exopolysaccharide was added (phase D). Lastly, the pH was adjusted to 6 by adding Triethanolamine 99 [INCI: Triethanolamine] drop by drop (phase E) obtaining a cosmetic composition with the proportions shown in table 1.

TABLE 1

|   | INGREDIENT | % in weight |
|---|---|---|
| A | Water | 77.05 |
| A | Phenonip ™ | 0.80 |
| A | Abiol | 0.30 |
| A | Propylene Glycol | 2.00 |
| C | Lipomulse 165 | 6.00 |
| C | Alcohol CO-1695 | 0.70 |
| C | Edenor ™ L2SM | 1.80 |

TABLE 1-continued

| | INGREDIENT | % in weight |
|---|---|---|
| C | Caprylic Capric Triglycerides | 8.00 |
| C | Massocare HD | 3.00 |
| B | Carbopol ® ETD 2020 | 0.25 |
| D | Exopolysaccharide of strain CNCM I-4150 | 0.01 |
| D | Sodium salicylate | 0.005 |
| D | Water | 0.085 |
| E | Triethanolamine 99 | q.s. |

Example 4: Preparation of a Cosmetic Composition of the Exopolysaccharide Excreted by Bacterial Strain CNCM I-4150

The cosmetic composition of this example was prepared following the instructions for the preparation of the composition of example 3 with the same ingredients, but using the quantities in table 2.

TABLE 2

| | INGREDIENT | % in weight |
|---|---|---|
| A | Water | 76.10 |
| A | Phenonip ™ | 0.80 |
| A | Abiol | 0.30 |
| A | Propylene Glycol | 2.00 |
| C | Lipomulse ™ 165 | 6.00 |
| C | Alcohol CO-1695 | 0.70 |
| C | Edenor ™ L2SM | 1.80 |
| C | Caprylic Capric Triglycerides | 8.00 |
| C | Massocare ™ HD | 3.00 |
| B | Carbopol ® ETD 2020 | 0.30 |
| D | Exopolysaccharide of strain CNCM I-4150 | 0.10 |
| D | Sodium salicylate | 0.05 |
| D | Water | 0.85 |
| E | Triethanolamine 99 | q.s. |

Example 5: Comparative Study of Water Retention Between the Hyaluronic Acid and the Exopolysaccharide of Strain CNCM I-4150

This example studies the changes to the weight over time at any level of relative humidity between 0 and 95% for a sample of exopolysaccharide of bacterial strain CNCM I-4150 compared with hyaluronic acid.

The experiments were carried out with the dynamic vapor sorption technique (DVS), with a TA Instruments Q5000 SA thermogravimetric analyzer (TGA), treating the values obtained with the Universal Analysis 2000 version 4.5 A (TA Instruments). The protocol used considers an initial equilibrium step at 60° C., establishing humidity at 0.0%, and a subsequent equilibrium at 33° C., from which the relative humidity is begun to be raised in 10% stages. Once 95% has been reached successive stages of lowering the relative humidity are carried out. Throughout the whole period of variation of the relative humidity the weight of the exopolysaccharide is recorded. Afterwards the same experiment was carried out under the same conditions with hyaluronic acid.

The results of the studies carried out showed that the exopolysaccharide of the invention shows a better water retention profile than hyaluronic acid (FIG. 1). Calculating water retention at the point of maximum relative humidity (95%), the value obtained by the exopolysaccharide was 12.7% greater than that obtained with hyaluronic acid.

Example 6: In Vivo Study of Skin Hydration

A comparative in vivo study of the hydrating capacity of the skin of the cosmetic composition in example 4 and its placebo composition, which contained the same ingredients and in the same percentages as the composition of example 4, except the exopolysaccharide of strain CNCM I-4150, which was substituted by water.

The measurements of this study were carried out in a bioclimatic room (24±2° C.; 50±10% relative humidity) with the purpose of maintaining the temperature and humidity constant during the measuring. The measurements of skin hydration were carried out on the cheeks using a Corneometer CM 825 (Courage & Khazaka). Twenty women with an average age of 44.3 participated in the study; they were instructed not to apply any cosmetic or dermopharmaceutical composition other than those used in the study during its duration, or during the 24 hours prior to the beginning of the study.

All the volunteers applied a fixed quantity of 0.4 ml of the placebo composition on the right side of their faces and 0.4 ml of the cosmetic composition from example 4 on the left side of their faces twice a day for 20 days, always applying the placebo composition to the right side and the composition from example 4 to the left side of their faces. The volunteers did not apply any cosmetic composition to their faces for at least 12 hours before undertaking the instrumental measurements.

The skin hydration measurements were carried out 2 and 8 hours after the first application of the previous compositions as well as 20 days after the beginning of the study.

Table 3 shows the average percentages of improvement to the skin's hydration of the placebo composition and the cosmetic composition from example 4 containing the exopolysaccharide of strain CNCM I-4150.

TABLE 3

| | $T_{2\ hours} - T_0$ | $T_{8\ hours} - T_0$ | $T_{20\ days} - T_0$ |
|---|---|---|---|
| Placebo composition | 12.1% | 7.1% | 0% |
| Composition from example 4 | 36.8% | 30.8% | 37.2% |

The results in the table clearly show that the composition from example 4 has greater skin hydration power than the placebo composition, and therefore it is demonstrated that the exopolysaccharide described in this invention improves the skin's hydration.

Example 7: In Vivo Study of Reduction of the Skin's Roughness

A comparative in vivo study of the capacity of reducing the roughness of the skin, i.e., anti-wrinkle effect, of the cosmetic composition from example 3 and its placebo composition, which contained the same ingredients and in the same percentages as the composition from example 3 except the exopolysaccharide of strain CNCM I-4150, which was substituted by water.

The measurements for this study were carried out in a bioclimatic room (24±2° C.; 50±10% relative humidity) in order to maintain a constant temperature and humidity during the measurements. The measurements of the skin's roughness were carried out through silicon replicas of the skin using adhesive discs (3M, 24×40) and a quick-setting synthetic polymer (SILFLO, Flexico Ltd). The silicon replicas of the skin were analyzed using image processing software (Quantilines, Monaderm) which enabled maximum value of roughness to be determined (depth of the wrinkle, referred to in the study as Rz). The anti-wrinkle effectiveness is shown by a decrease in the Rz value. Twenty women with an average age of 41 participated in the study; they were instructed not to apply any cosmetic or dermopharmaceutical composition other than those used in the study during its duration, or during the 24 hours prior to the beginning of the study.

All the volunteers applied a fixed quantity of 0.4 ml of the placebo composition on the right side of their faces and 0.4 ml of the cosmetic composition from example 3 on the left side of their faces twice a day for 20 days, always applying the placebo composition to the right side and the composition from example 4 to the left side of their faces. The volunteers did not apply any cosmetic composition to their faces for at least 12 hours before undertaking the instrumental measurements.

The skin replicas were carried out 2 and 8 hours after the first application of the previous compositions, as well as 20 days after the beginning of the study. Table 4 shows the average percentages of percentage reduction of the maximum roughness (Rz) of the skin from the placebo composition and the cosmetic composition from example 3 containing the exopolysaccharide of strain CNCM I-4150.

TABLE 4

|  | $T_{2\ hours} - T_0$ | $T_{8\ hours} - T_0$ | $T_{20\ days} - T_0$ |
|---|---|---|---|
| Placebo composition | −0.1% | 5.6% | 3.9% |
| Composition from example 3 | −11.1% | −8.4% | −9.3% |

The results from table 4 clearly show that the composition from example 3 has a lowering effect on the maximum roughness Rz, and therefore it is demonstrated that the exopolysaccharide described in this invention has an anti-wrinkle effect.

Prophetic Example 8: Preparation of a Cosmetic Composition of the Exopolysaccharide Excreted by Bacterial Stain CNCM I-4150 and Antarcticine®

The cosmetic composition from this example is prepared by following the instructions for the preparation of the composition from example 3 with the ingredients and the quantities from table 5. In the preparation of phase D Antarcticine® [INCI: *Pseudoalteromonas* Ferment Extract] is also added with sodium salicylate [INCI: Sodium Salicylate].

TABLE 5

|  | INGREDIENT | % in weight |
|---|---|---|
| A | Water | 75.59 |
| A | Phenonip ™ | 0.80 |
| A | Abiol | 0.30 |
| A | Propylene Glycol | 2.00 |
| C | Lipomulse ™ 165 | 6.00 |
| C | Alcohol CO-1695 | 0.70 |
| C | Edenor ™ L2SM | 1.80 |
| C | Caprylic Capric Triglycerides | 8.00 |
| C | Massocare ™ HD | 3.00 |
| B | Carbopol ® ETD 2020 | 0.30 |
| D | Exopolysaccharide of strain CNCM I-4150 | 0.10 |
| D | Antarcticine ® | 0.10 |
| D | Sodium salicylate | 0.06 |
| D | Water | 1.25 |
| E | Triethanolamine 99 | q.s. |

Prophetic Example 9: Preparation of a Cosmetic Composition of the Exopolysaccharide Excreted by Bacterial Strain CNCM I-4150 and Serilesine®

The cosmetic composition from this example is prepared by following the instructions for the preparation of the composition from example 3 with the ingredients and quantities of table 6. In the preparation of phase D Serilesine® [INCI: Hexapeptide-10] is also added.

TABLE 6

|  | INGREDIENT | % in weight |
|---|---|---|
| A | Water | 76.00 |
| A | Phenonip ™ | 0.80 |
| A | Abiol | 0.30 |
| A | Propylene Glycol | 2.00 |
| C | Lipomulse ™ 165 | 6.00 |
| C | Alcohol CO-1695 | 0.70 |
| C | Edenor ™ L2SM | 1.80 |
| C | Caprylic Capric Triglycerides | 8.00 |
| C | Massocare ™ HD | 3.00 |
| B | Carbopol ® ETD 2020 | 0.30 |
| D | Exopolysaccharide of strain CNCM I-4150 | 0.10 |
| D | Serilesine ® | 0.10 |
| D | Sodium salicylate | 0.05 |
| D | Water | 0.85 |
| E | Triethanolamine | q.s. |

Prophetic Example 10: Preparation of Liposomes Containing the Exopolysaccharide Excreted by Bacterial Strain CNCM I-4150 Bound to Cationic Polymers of Polyquaternium-16

In a suitable vessel the exopolysaccharide obtained according to example 1 in water [INCI: Water (Aqua)] is added with sodium salicylate [INCI: Sodium Salicylate] and phase A is obtained. Water, Zemea™ Propanediol [INCI: Propanediol] and phenoxyethanol are added to this phase (phases B to D). When all the previous components have been dissolved Leciflor 100 IP [INCI: Lecithin] is added (phase E) little by little under intense stirring until complete dissolution. Afterwards Labrasol [INCI: PEG-8 Caprylic/Capric Glycerides] is added (phase F) and is left stirring for 10-15 minutes in order to form an emulsion.

TABLE 7

|  | INGREDIENT | % in weight |
|---|---|---|
| A | Water | 6 |
| A | Sodium salicylate | 0.03 |
| A | Exopolysaccharide of strain CNCM I-4150 | 1.5 |
| B | Water | q.s.p. 100 |
| C | Zemea ™ Propanediol | 8.50 |
| D | Phenoxyethanol | 1.70 |
| E | Leciflor ™ 100 IP | 10.00 |
| F | Labrasol ™ | 4.00 |

The sample is passed through a microfluidifier for one cycle at an entrance pressure of 80 bar and 12500 psi on exit. The liposomes obtained are added to Luviquat® HM 552 [INCI: Polyquaternium-16] in a liposome:cationic polymer ratio of 1.5:1 under light stirring.

Prophetic Example 11: Preparation of Coacervation Capsules of Lipid Nanoparticles Containing a Microemulsion of the Exopolysaccharide Excreted by Bacterial Strain CNCM I-4150

Docusate Sodium USP [INCI: Diethylhexyl Sodium Sulfosuccinate] and Prisorine™ 3505 [INCI: Isostearic Acid]

are mixed together in a suitable vessel (phase A). In another vessel the exopolysaccharide obtained according to example 1 is dissolved in ethanol partially denatured with phthalate-Bitrex [INCI: Alcohol Denat.]. Once dissolved, the water is added (phase B).

Phase B is slowly added to phase A under stirring. In a vessel the mixture of phases A and B is added to the phase C ingredients, refined soybean oil IP Ph. Eur [INCI: *Glycine Soja* (Soybean) Oil], Arlacel 83V [INCI: Sorbitan Sesquioleate], and Massocare HD [INCI: Isohexadecane] (phase C) and a microemulsion is obtained.

In another suitable vessel the following ingredients are added in this order: water, Amigel® [INCI: Sclerotium Gum], Argireline® [INCI: Acetyl Hexapeptide-8], Zemea™ Propanediol [INCI: Propanediol] and phenoxyethanol [INCI: Phenoxyethanol] (phase D), and are stirred until fully homogenized.

Next, the mixture of ingredients D is added to phases A, B and C, under turbine stirring until an emulsion is formed.

Lastly, the mixture is homogenized under pressure in a microfluidifier for 3 cycles with an entrance pressure of 80 bar and pressure on exit of 15000 psi. Throughout the whole process the sample is maintained thermostated at 25° C. using a water/glycol refrigeration circuit.

TABLE 8

| | INGREDIENT | % in weight |
|---|---|---|
| A | Docusate Sodium USP | 1.08 |
| A | Prisorine ™ 3505 | 6.10 |
| B | Exopolysaccharide of strain CNCM I-4150 | 0.02 |
| B | Ethanol partially denatured with phthalate-Bitrex | 0.24 |
| B | Water | 0.56 |
| C | Refined soybean oil IP Ph. Eur. | 12.00 |
| C | Arlacel ™ 83V | 4.30 |
| C | Massocare ™ HD | 5.50 |
| D | Water | q.s.p. 100 |
| D | Amigel ® | 0.50 |
| D | Argireline ® | 0.01 |
| D | Zemea ™ Propanediol | 5.00 |
| D | Phenoxyethanol | 2.6 |

The invention claimed is:

1. A cosmetic or dermopharmaceutical composition for the treatment or care of at least one of skin, mucous membranes, hair, and nails, the composition comprising an effective amount of a modified exopolysaccharide, wherein the modified exopolysaccharide is isolated from a strain of *Pseudoalteromonas* sp. with deposit number CNCM I-4150, and modified by radical depolymerization resulting in a polymer with a molecular weight between 100 and 100,000 Daltons, the modified exopolysaccharide comprising mannose, glucose, glucuronic acid, galacturonic acid, galactose, and N-acetylglucosamine, and at least one of the group consisting of a cosmetically or dermopharmaceutically acceptable excipient, a cosmetically or dermopharmaceutically acceptable adjuvant, and a cosmetically or dermopharmaceutically acceptable ingredient.

2. The composition according to claim 1, wherein the modified exopolysaccharide contains, by weight, 3% to 12% of mannose, 12% to 34% of glucose, 12% to 34% of glucuronic acid, 2% to 20% of galacturonic acid, 12% to 34% of galactose and 2% to 18% of N-acetylglucosamine, with the condition that the sum of the percentages does not exceed 100%.

3. The cosmetic or dermopharmaceutical composition according to claim 1, wherein the modified exopolysaccharide is at a concentration of between 0.00000001% and 20% by weight of a total weight of the composition.

4. The cosmetic or dermopharmaceutical composition of claim 1, wherein the composition is present in a formulation for oral administration for the treatment or care of the mucous membranes, the formulation being selected from the group consisting of capsules, gelatin capsules, soft capsules, hard capsules, tablets, powders, granules, chewing gum, solutions, suspensions, emulsions, syrups, polysaccharide films, jellies, and gelatin.

5. The cosmetic or dermopharmaceutical composition according to claim 1, wherein the at least one of the excipient, adjuvant and ingredient is selected from the group consisting of agents inhibiting acetylcholine receptor clustering, muscle contraction inhibiting agents, anticholinergic agents, elastase inhibiting agents, matrix metalloprotease inhibiting agents, melanin synthesis stimulating or inhibiting agents, whitening or depigmenting agents, propigmenting agents, self-tanning agents, antiaging agents, NO-synthase inhibiting agents, 5α-reductase inhibiting agents, lysyl- and/or prolyl hydroxylase inhibiting agents, antioxidants, free radical scavengers and/or agents against atmospheric pollution, reactive carbonyl species scavengers, anti-glycation agents, antihistamine agents, antiviral agents, antiparasitic agents, emulsifiers, emollients, organic solvents, liquid propellants, skin conditioners, humectants, substances that retain moisture, alpha hydroxyacids, beta hydroxyacids, moisturizers, epidermal hydrolytic enzymes, vitamins, amino acids, proteins, pigments or colorants, dyes, gelling polymers, thickeners, surfactants, softening agents, anti-wrinkle/antiaging agents, agents able to reduce or treat bags under the eyes, exfoliating agents, desquamating agents, keratolytic agents, antimicrobial agents, antifungal agents, fungistatic agents, bactericidal agents, bacteriostatic agents, agents stimulating the synthesis of dermal or epidermal macromolecules and/or capable of inhibiting or preventing their degradation, collagen synthesis-stimulating agents, elastin synthesis-stimulating agents, decorin synthesis-stimulating agents, laminin synthesis-stimulating agents, defensin synthesis-stimulating agents, aquaporin synthesis-stimulation agents, hyaluronic acid synthesis-stimulating agents, fibronectin synthesis-stimulating agents, sirtuin synthesis-stimulating agents, chaperone synthesis-stimulating agents, agents stimulating the synthesis of lipids and components of the stratum corneum, ceramides, fatty acids, agents that inhibit collagen degradation, agents that inhibit elastin degradation, agents that inhibit serine proteases, agents stimulating fibroblast proliferation, agents stimulating keratinocyte proliferation, agents stimulating adipocyte proliferation, agents stimulating melanocyte proliferation, agents stimulating keratinocyte differentiation, agents stimulating adipocyte differentiation, agents that inhibit acetylcholinesterase, skin relaxant agents, glycosaminoglycan synthesis-stimulating agents, anti-hyperkeratosis agents, comedolytic agents, anti-psoriasis agents, DNA repairing agents, DNA protecting agents, stabilizers, anti-itching agents, agents for the treatment and/or care of sensitive skin, firming agents, redensifying agents, restructuring agents, anti-stretch mark agents, binding agents, agents regulating sebum production, lipolytic agents or agents stimulating lipolysis, anti-cellulite agents, antiperspirant agents, agents stimulating healing, coadjuvant healing agents, agents stimulating reepithelialization, coadjuvant reepithelialization agents, cytokine growth factors, calming agents, anti-inflammatory agents and/or analgesics, anesthetic agents, agents acting on capillary circulation and/or microcirculation, agents stimulating angiogenesis, agents that inhibit vascular permeability, venotonic agents, agents acting on cell metabolism, agents to improve dermal-epidermal junction, agents inducing hair growth, hair growth inhibiting or retardant agents, agents delaying hair loss, preservatives, perfumes, chelating agents, vegetable extracts, essential oils, marine extracts, agents obtained from a biofermentation process, mineral salts, cell extracts and sunscreens, and organic or mineral photoprotective agents active against at least one of ultraviolet A and ultraviolet B rays.

6. The cosmetic or dermopharmaceutical composition according to claim 1, formulated as one of the group consisting of multiple emulsions, oil and/or silicone-in-water emulsions, water-in-oil and/or silicone emulsions, water/oil/water emulsions, water/silicone/water or oil/water/oil type emulsions, silicone/water/silicone type emulsions, microemulsions, emulsions, solutions, liquid crystals, anhydrous compositions, aqueous dispersions, oils, milks, balsams, foams, aqueous lotions, oily lotions, aqueous gels, oily gels, creams, hydroalcoholic solutions, hydroglycolic solutions, hydrogels, liniments, sera, soaps, shampoos, conditioners, face masks, hairsprays, serums, polysaccharide films, ointments, mousses, pomades, pastes, powders, bars, pencils, sprays, and aerosols.

7. A solid organic polymer or solid mineral support comprising an effective amount of the cosmetic or dermopharmaceutical composition according to claim 1 absorbed thereto, wherein the solid organic polymer or solid mineral support is selected from the group consisting of talc, bentonite, silica, starch and maltodextrin.

8. A fabric, non-woven fabric, or medical device comprising an effective amount of the cosmetic or dermopharmaceutical composition according to claim 1 incorporated therein.

9. A cosmetic or dermopharmaceutical composition comprising a modified exopolysaccharide, wherein the modified exopolysaccharide is isolated from a strain of *Pseudoalteromonas* sp. with deposit number CNCM I-4150 and modified by radical depolymerization resulting in a polymer with a molecular weight between 100 and 100,000 Daltons, in an effective quantity for cosmetic or dermopharmaceutical treatment or care of at least one of skin, mucous membranes, hair and nails, and at least one of the group consisting of a cosmetically or dermopharmaceutically acceptable excipient, a cosmetically or dermopharmaceutically acceptable adjuvant, and a cosmetically or dermopharmaceutically acceptable ingredient,
wherein the modified exopolysaccharide is incorporated into a cosmetically or dermopharmaceutically acceptable delivery system or sustained release system, or
wherein the cosmetic or dermopharmaceutical composition is absorbed on a solid organic polymer or solid mineral support selected from the group consisting of talc, bentonite, silica, starch and maltodextrin, or
wherein the cosmetic or dermopharmaceutical composition is incorporated into a fabric, non-woven fabric or medical device.

10. The composition according to claim 9, wherein the modified exopolysaccharide comprises at least four different neutral monosaccharides and two different acid monosaccharides.

11. The composition according to claim 10, wherein the four different neutral monosaccharides are mannose, glucose, galactose and N-acetylglucosamine.

12. The composition according to claim 10, wherein the two different acid monosaccharides are glucuronic acid and galacturonic acid.

13. A cosmetic or dermopharmaceutical composition for the treatment or care of at least one of skin, mucous membranes, hair, and nails, the composition comprising an effective amount of a modified exopolysaccharide, wherein the modified exopolysaccharide is isolated from a strain of *Pseudoalteromonas* sp. with deposit number CNCM I-4150 and modified by radical depolymerization resulting in a polymer with a molecular weight between 100 and 100,000 Daltons, the modified exopolysaccharide comprising mannose, glucose, glucuronic acid, galacturonic acid, galactose, and N-acetylglucosamine, and at least one of the group consisting of a cosmetically or dermopharmaceutically acceptable excipient, a cosmetically or dermopharmaceutically acceptable adjuvant, and a cosmetically or dermopharmaceutically acceptable ingredient, the composition being formulated as one of the group consisting of multiple emulsions, oil and/or silicone-in-water emulsions, water-in-oil and/or silicone emulsions, water/oil/water emulsions, water/silicone/water or oil/water/oil type emulsions, silicone/water/silicone type emulsions, microemulsions, emulsions, liquid crystals, anhydrous compositions, oils, balsams, foams, oily lotions, aqueous gels, oily gels, creams, hydroalcoholic solutions, hydroglycolic solutions, hydrogels, soaps, shampoos, hairsprays, polysaccharide films, ointments, mousses, pomades, pastes, powders, bars, pencils, sprays, and aerosols.

14. A method of treatment or care of at least one of skin, mucous membranes, hair and nails of a subject in need thereof, the method comprising administering to the at least one of the skin, mucous membranes, hair and nails of said subject an effective amount of the cosmetic or dermopharmaceutical composition of claim 1.

15. The method according to claim 14, wherein said administering is carried out by topical, transdermal, oral, or parental administration.

16. The method according to claim 14, wherein the modified exopolysaccharide is prepared by a process comprising the fermentation of the bacterial strain CNCM I-4150 of *Pseudoalteromonas* sp.

17. The method according to claim 14, wherein the modified exopolysaccharide is incorporated into a cosmetically or dermopharmaceutically acceptable delivery system or sustained release system.

18. The method according to claim 14, wherein the cosmetic or dermopharmaceutical composition is absorbed on a solid organic polymer or solid mineral support selected from the group formed by talc, bentonite, silica, starch and maltodextrin.

19. The method according to claim 14, wherein the cosmetic or dermopharmaceutical composition is incorporated into a fabric, non-woven fabric or medical device.

20. The method according to claim 14, wherein the cosmetic or dermopharmaceutical composition is included in a formulation selected from the group consisting of multiple emulsions, oil and/or silicone-in-water emulsions, water-in-oil and/or silicone emulsions, water/oil/water or water/silicone/water type emulsions, oil/water/oil or silicone/water/silicone type emulsions, microemulsions, emulsions, solutions, liquid crystals, anhydrous compositions, aqueous dispersions, oils, milks, balsams, foams, aqueous lotions, oily lotions, aqueous gels, oily gels, creams, hydroalcoholic solutions, hydroglycolic solutions, hydrogels, liniments, sera, soaps, shampoos, conditioners, face masks, hairsprays, serums, polysaccharide films, ointments, mousses, pomades, pastes, powders, bars, pencils, sprays, and aerosols.

21. The method according to claim 14, wherein the cosmetic or dermopharmaceutical composition is included in a formulation for oral administration which is selected from the group consisting of capsules, gelatin capsules, soft capsules, hard capsules, tablets, powders, granules, chewing gum, solutions, suspensions, emulsions, syrups, polysaccharide films, jellies and gelatin.

22. The method according to claim 14, wherein the at least one cosmetically or dermopharmaceutically acceptable excipient, adjuvant or ingredient is selected from the group consisting of agents inhibiting acetylcholine receptor clustering, muscle contraction inhibiting agents, anticholinergic agents, elastase inhibiting agents, matrix metalloprotease inhibiting agents, melanin synthesis stimulating or inhibiting agents, whitening or depigmenting agents, propigmenting agents, self-tanning agents, antiaging agents, NO-synthase inhibiting agents, 5α-reductase inhibiting agents, lysyl- and/or prolyl hydroxylase inhibiting agents, antioxidants, free radical scavengers and/or agents against atmospheric pollution, reactive carbonyl species scavengers, anti-glycation agents, antihistamine agents, antiviral agents, antiparasitic agents, emulsifiers, emollients, organic solvents, liquid propellants, skin conditioners, humectants, substances that retain moisture, alpha hydroxyacids, beta hydroxyacids, moisturizers, epidermal hydrolytic enzymes, vitamins, amino acids, proteins, pigments or colorants, dyes, gelling polymers, thickeners, surfactants, softening agents, anti-wrinkle/antiaging agents, agents able to reduce or treat bags under the eyes, exfoliating agents, desquamating agents, keratolytic agents, antimicrobial agents, antifungal agents, fungistatic agents, bactericidal agents, bacteriostatic agents, agents stimulating the synthesis of dermal or epidermal macromolecules and/or capable of inhibiting or preventing their degradation, collagen synthesis-stimulating agents, elastin synthesis-stimulating agents, decorin synthesis-stimulating agents, laminin synthesis-stimulating agents, defensin synthesis-stimulating agents, aquaporin synthesis-stimulation agents, hyaluronic acid synthesis-stimulating agents, fibronectin synthesis-stimulating agents, sirtuin synthesis-stimulating agents, chaperone synthesis-stimulating agents, agents stimulating the synthesis of lipids and components of the stratum corneum, ceramides, fatty acids, agents that inhibit collagen degradation, agents that inhibit elastin degradation, agents that inhibit serine proteases, agents stimulating fibroblast proliferation, agents stimulating keratinocyte proliferation, agents stimulating adipocyte proliferation, agents stimulating melanocyte proliferation, agents stimulating keratinocyte differentiation, agents stimulating adipocyte differentiation, agents that inhibit acetylcholinesterase, skin relaxant agents, glycosaminoglycan synthesis-stimulating agents, anti-hyperkeratosis agents, comedolytic agents, anti-psoriasis agents, DNA repairing agents, DNA protecting agents, stabilizers, anti-itching agents, agents for the treatment and/or care of sensitive skin, firming agents, redensifying agents, restructuring agents, anti-stretch mark agents, binding agents, agents regulating sebum production, lipolytic agents or agents stimulating lipolysis, anti-cellulite agents, antiperspirant agents, agents stimulating healing, coadjuvant healing agents, agents stimulating reepithelialization, coadjuvant reepithelialization agents, cytokine growth factors, calming agents, anti-inflammatory agents and/or analgesics, anesthetic agents, agents acting on capillary circulation and/or microcirculation, agents stimulating angiogenesis, agents that inhibit vascular permeability, venotonic agents, agents acting on cell metabolism, agents to improve dermal-epidermal junction, agents inducing hair growth, hair growth inhibiting or retardant agents, agents delaying hair loss, preservatives, perfumes, chelating agents, vegetable extracts, essential oils, marine extracts, agents obtained from a biofermentation process, mineral salts, cell extracts and sunscreens, and organic or mineral photoprotective agents active against at least one of ultraviolet A and B rays.

23. The method according to claim 14, wherein the treatment or care reduces or delays signs of aging.

24. The method according to claim 23, wherein the treatment or care which reduces or delays the signs of aging is a treatment or care of wrinkles on the skin and/or dryness of the skin.

25. The method according to claim 14, wherein the treatment or care is a treatment or care of a condition, disorder or disease of mammals which is a consequence of a lack or decrease in the hydration of the skin, mucous membranes, hair or nails.

26. The method according to claim 25, wherein the conditions, disorders or diseases which are a consequence of a lack or decrease in the hydration of the skin, mucous membranes, hair and/or nails are selected from the group consisting of dry skin, xerosis, hyperkeratosis, reactive hyperkeratosis, palmar and plantar hyperkeratosis, corns and calluses, actinic keratosis, non-actinic keratosis, atopic dermatitis, contact eczema, seborrheic dermatitis, dandruff, cradle cap on babies, acne, rosacea, nevus, ichthyosis, psoriasis, parakeratosis, pityriasis, lichen planus, palmoplantar keratoderma, chapped lips, vaginal dryness, ocular dryness, dry hair, and brittle hair and nails.

27. A method of treatment or care of at least one of skin, mucous membranes, hair and nails of a subject in need thereof, the method comprising administering to the at least one of the skin, mucous membranes, hair and nails of said subject an effective amount of the cosmetic or dermopharmaceutical composition of claim 13.

28. A method for preparing a composition comprising modified exopolysaccharide, the method comprising fermenting bacterial strain CNCM 1-4150 of *Pseudoalteromonas* sp, isolating an exopolysaccharide therefrom, the exopolysaccharide comprising mannose, glucose, glucuronic acid, galacturonic acid, galactose, and N-acetylglucosamine, modifying the exopolysaccharide by radical depolymerization resulting in a polymer with a molecular weight between 100 and 100,000 Daltons, and combining the isolated modified exopolysaccharide with at least one of the group consisting of a cosmetically or dermopharmaceutically acceptable excipient, a cosmetically or dermopharmaceutically acceptable adjuvant, and a cosmetically or dermopharmaceutically acceptable ingredient.

* * * * *